(12) United States Patent
Chekmenev et al.

(10) Patent No.: US 10,338,052 B2
(45) Date of Patent: Jul. 2, 2019

(54) METHODS OF DETECTING SULFUR-CONTAINING COMPOUNDS

(71) Applicant: Vanderbilt University, Nashville, TN (US)

(72) Inventors: Eduard Y. Chekmenev, Brentwood, TN (US); Roman V. Shchepin, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 368 days.

(21) Appl. No.: 15/362,846

(22) Filed: Nov. 29, 2016

(65) Prior Publication Data

US 2017/0153218 A1 Jun. 1, 2017

Related U.S. Application Data

(60) Provisional application No. 62/260,960, filed on Nov. 30, 2015.

(51) Int. Cl.
*G01N 33/28* (2006.01)
*G01N 24/08* (2006.01)
(Continued)

(52) U.S. Cl.
CPC .......... *G01N 33/287* (2013.01); *G01N 24/08* (2013.01); *G01R 33/282* (2013.01); *G01R 33/307* (2013.01)

(58) Field of Classification Search
None
See application file for complete search history.

(56) References Cited

U.S. PATENT DOCUMENTS 5,498,960 A 3/1996 Vinegar et al.
6,661,226 B1 12/2003 Hou et al.
(Continued)

FOREIGN PATENT DOCUMENTS

WO 9612976 A1 5/1996
WO 2008155093 A1 12/2008
WO 2013102916 A1 7/2013

OTHER PUBLICATIONS

"United States Environment Protection Agency, Office of Transportation and Air Quality, EPA-420-F-14-007, 2014."
(Continued)

*Primary Examiner* — Jermele M Hollington
(74) *Attorney, Agent, or Firm* — Meunier Carlin & Curfman LLC

(57) ABSTRACT

Methods of detecting a sulfur-containing compound in a sample are described, for example using NMR-SABRE hyperpolarization of the sulfur-containing compounds in the sample. The methods can comprise, for example, contacting a sample comprising a sulfur-containing compound with parahydrogen and a catalyst to form a mixture. A spin order can be transferred from the parahydrogen to the sulfur-containing compound thereby hyperpolarizing the sulfur-containing compound during a temporary association of the parahydrogen, the sulfur-containing compound, and the catalyst. The methods can further comprise, for example, performing an NMR measurement on the mixture comprising the hyperpolarized sulfur-containing compound to detect the hyperpolarized sulfur-containing compound (e.g., from the hyperpolarized NMR signals. In some examples, the methods described herein can be used for detecting a sulfur-containing contaminant in a fuel.

20 Claims, 11 Drawing Sheets

(51) Int. Cl.
  *G01R 33/28*   (2006.01)
  *G01R 33/30*   (2006.01)

(56) References Cited

U.S. PATENT DOCUMENTS

| | | | |
|---|---|---|---|
| 7,501,236 | B1 | 3/2009 | Knox et al. |
| 8,154,284 | B2 | 4/2012 | Duckett et al. |
| 8,825,132 | B2 | 9/2014 | Lohman et al. |
| 9,081,071 | B2 | 7/2015 | Tang et al. |
| 9,086,359 | B2 | 7/2015 | Wiley et al. |
| 2010/0219826 | A1* | 9/2010 | Duckett ............... A61K 49/06 324/307 |
| 2011/0233089 | A1 | 9/2011 | Verk et al. |
| 2011/0274626 | A1 | 11/2011 | Duckett et al. |
| 2014/0034481 | A1 | 2/2014 | Waddell et al. |
| 2015/0106027 | A1 | 4/2015 | Koseoglu et al. |

OTHER PUBLICATIONS

Abragam, et al., "Principles of dynamic nuclear polarisation", Prog. Phys 41, 1978, 395-467.
Adams, et al., "A theoretical basis for spontaneous polarization transfer in non-hydrogenative parahydrogen-induced polarization.", J. Chem. Phys. 131, 194505, 2009, 15 pages.
Adams, et al., "Reversible interactions with para-hydrogen enhance NMR sensitivity by polarization transfer", Science 323, 2009, 1708-1711.
Ardenkjaer-Larsen, et al., "Increase in signal-to-noise ratio of >10,000 times in liquid-state NMR", Proc. Natl. Acad. Sci. U. S. A. 100, 2003, 10158-10163.
Barskiy, et al., "The Feasibility of Formation and Kinetics of NMR Signal Amplification by Reversible Exchange (SABRE) at High Magnetic Field (9.4 T)", J. Am. Chem. Soc. 136, 2014, 3322-3325.
Barskiy, et al., "A simple analytical model for signal amplification by reversible exchange (SABRE) process", Phys. Chem. Chem. Phys. 18, 2016, 89-93.
Barskiy, et al., "In Situ and Ex Situ Low-Field NMR Spectroscopy and MRI Endowed by SABRE Hyperpolarization", ChemPysChem 15, 2014, 4100-4107.
Barskiy, et al., "Over 20% (15)N Hyperpolarization in Under One Minute for Metronidazole, an Antibiotic and Hypoxia Probe.", J Am Chem Soc. 138(26) 2016, 8080-3, doi: 10.1021/jacs.6b04784.
Bowers, et al., J. Am. Chem. Soc. 109, 1987, 5541-5542.
Bowers, et al., "Transformation of symmetrization order to nuclear-spin magnetization by chemical reaction and nuclear magnetic resonance.", Phys. Rev. Lett. 57, 1986, 2645-2648.
Brindle, et al., "Imaging metabolism with hyperpolarized (13)C-labeled cell substrates", J. Am. Chem. Soc. 137, 2015, 6418-6427.
Coffey, et al., "High-Resolution Low-Field Molecular Magnetic Resonance Imaging of Hyperpolarized Liquids", Anal. Chem. 86, 2014, 9042-9049.
Coffey, et al., "Low-field MRI can be more sensitive than high-field MRI." J. Magn. Reson. 237, 2013, 169-174.
Comment, et al., "Hyperpolarized Magnetic Resonance as a Sensitive Detector of Metabolic Function", Biochemistry 53, 2014, 7333-7357.
Coomes, "Daily Environment Report, Bloomberg", http://www.bna.com/epa-tier-rule-n17179882576/, 2014, 10 pages.
Cowley, et al., "Iridium N-Heterocyclic Carbene Complexes as Efficient Catalysts for Magnetization Transfer from para-Hydrogen", J. Am. Chem. Soc. 133, 2011, 6134-6137.
Eshuis, et al., "Determination of long-range scalar (1)H-(1)H coupling constants responsible for polarization transfer in SABRE.", J. Magn. Reson. 265, 2016, 59-66.
Eshuis, et al., "Quantitative trace analysis of complex mixtures using SABRE hyperpolarization", Angew. Chem. Int. Ed. 54, 2015, 1481-1484.
Eshuis, et al., "Toward Nanomolar Detection by NMR Through SABRE Hyperpolarization", J. Am. Chem. Soc. 136, 2014, 2695-2698.
Gloggler, et al., "Para-hydrogen induced polarization of amino acids, peptides and deuterium—hydrogen gas", Phys. Chem. Chem. Phys. 13, 2011, 13759-13764.
Goodson, et al., "Nuclear magnetic resonance of laser-polarized noble gases in molecules, materials, and organisms.", J. Magn. Reson. 155, 2002, 157-216.
Hermkens, et al., "NMR-Based Chemosensing via p-H2 Hyperpolarization: Application to Natural Extracts", Anal. Chem. 88, 2016, 3406-3412.
Ho, et al., "Deep HDS of diesel fuel: chemistry and catalysis", Catal. Today 98, 2004, 3-18.
Hovener, et al., "A hyperpolarized equilibrium for magnetic resonance", Nat. Commun. 2013, 4, 5., 2013, 5 pages.
Kelemen, et al., "Direct Characterization of Kerogen by X-ray and Solid-State 13C Nuclear Magnetic Resonance Methods", Energy Fuels 21:3, 2007, 1548-1561.
Kelemen, et al., "Thermal Transformations of Nitrogen and Sulfur Forms in Peat Related to Coalification", Energy Fuels 20 (2), 2006, 635-652.
Kropp, et al., "A review of the occurrence, toxicity, and biodegradation of condensed thiophenes found in petroleum.", Can. J. Microbiol. 44, 1998, 605-622.
Kurhanewicz, et al., "Analysis of cancer metabolism by imaging hyperpolarized nuclei: prospects for translation to clinical research.", Neoplasia 13, 2011, 81-97.
Nelson, et al., "Metabolic Imaging of Patients with Prostate Cancer Using Hyperpolarized [1-13C]Pyruvate", Sci. Transl . Med. 5(198), 198ra108. doi:10.1126/scitranslmed.3006070, 2013.
Nikolaou, et al., "NMR Hyperpolarization Techniques for Biomedicine", Chem. Eur. J. 21, 2015, 3156-3166.
Pravdivtsev, et al., "Level Anti-Crossings are a Key Factor for Understanding para-Hydrogen-Induced Hyperpolarization in SABRE Experiments", ChemPhysChem 14, 2013, 3327-3331.
Reile, et al., "NMR detection in biofluid extracts at sub-µM concentrations via para-H2 induced hyperpolarization", Analyst 141, 2016, 4001-4005.
Salnikov, et al., "A Mechanistic Study of Thiophene Hydrodesulfurization by the Parahydrogen-Induced Polarization Technique", ChemCatChem 7, 2015, 3508-3512.
Shchepin, et al., "15N Hyperpolarization of Imidazole-15N2 for Magnetic Resonance pH Sensing via SABRE-SHEATH", ACS Sens.1 (6), 2016, 640-644.
Shchepin, et al., "Efficient Synthesis of Nicotinamide-1-15N for Ultrafast NMR Hyperpolarization Using Parahydrogen", Bioconjugate Chem. 27, 2016, 878-882.
Shchepin, et al., "Hyperpolarization of Neat Liquids by NMR Signal Amplification by Reversible Exchange." J. Phys. Chem. Lett. 6, 2015, 1961-1967.
Shi, et al., "Nanoscale Catalysts for NMR Signal Enhancement by Reversible Exchange", J. Phys. Chem. C 119, 2015, 7525-7533.
Shi, et al., "Heterogeneous solution NMR signal amplification by reversible exchange." Angew. Chem. Int. Ed. 53, 2014, 7495-7498.
Suefke, et al., "External high-quality-factor resonator tunes up nuclear magnetic resonance.", Nat. Phys. 767-771, 2015, 767-771.
Theis, et al., "Direct and cost-efficient hyperpolarization of long-lived nuclear spin states on universal 15N2-diazirine molecular tags", Sci. Adv. 2, e1501438, 2016, 8 ages.
Theis, et al., "Microtesla SABRE Enables 10% Nitrogen-15 Nuclear Spin Polarization", J. Am. Chem. Soc. 137, 2015, 1404-1407.
Truong, et al., "15N Hyperpolarization by Reversible Exchange Using SABRE-Sheath", J Phy. Chem. C 119, 2015, 8786-8797.
Truong, et al. , "Irreversible Catalyst Activation Enables Hyperpolarization and Water Solubility for NMR Signal Amplification by Reversible Exchange", J. Phys. Chem. B 118 (48), 2014, 13882-13889.
Zhivonitko, et al., "Strong 31P nuclear spin hyperpolarization produced via reversible chemical interaction with parahydrogen", Chem. Comm 51, 2015, 2506-2509.

\* cited by examiner

METHODS OF DETECTING SULFUR-CONTAINING COMPOUNDS

CROSS-REFERENCE TO RELATED APPLICATIONS

This application claims the benefit of U.S. Provisional Application No. 62/260,960, filed Nov. 30, 2015, which is hereby incorporated herein by reference in its entirety.

STATEMENT OF GOVERNMENT SUPPORT

This invention was made with Government support under Grant No. W81XWH-12-1-0159/BC 112431 awarded by the Department of Defense, Grant Nos. 1 R21EB018014 and 1R21EB020323 awarded by the National Institute of Health, and Grant No. CHE-1416268 awarded by the National Science Foundation. The Government has certain rights in the invention.

BACKGROUND

Sulfur-containing compounds are common contaminants of crude oil and natural gas. While most sulfur-containing compounds are removed prior to refining the crude oil and natural gas, some sulfur-containing compounds end up in the refined products. Specific to gasoline, sulfur-containing compounds are eventually converted into sulfur oxide during the process of fuel combustion in vehicles and other devices. The sulfur oxide is toxic for humans as well as for catalytic converters used in most vehicles in the United States. The US EPA regulates sulfur in fuels, and the upper limit has been tightened over the years (from ~300 ppm before 2000 to the current EPA mandated level of ~30 ppm of sulfur). In 2017, the EPA plans to curb acceptable sulfur levels further down to 10 ppm from the current 30 ppm level. This can require developing better refining solutions for removal of sulfur-containing compounds from fuel. Moreover, it would also be desirable to develop a cost-efficient technology to detect sulfur-containing compounds at a part-per-million (ppm) level in an organic medium with chemical specificity. The systems and methods discussed herein address these and other needs.

SUMMARY

Disclosed herein are methods of detecting sulfur-containing compounds in a sample, for example using NMR-SABRE hyperpolarization of the sulfur-containing compounds in the sample. The methods can comprise, for example, contacting a sample comprising a sulfur-containing compound with parahydrogen and a catalyst to form a mixture. In some examples, parahydrogen can serve as a source of NMR hyperpolarization. In some examples, the catalyst can comprise a metal complex, such as a transition metal complex (e.g., an iridium complex).

The sulfur-containing compound can comprise, for example, an organosulfur compound. In some examples, the organosulfur compound can comprise a sulfur-containing heterocycle, such as a thiophene compound. For example, the organosulfur compound can include thiophene, benzothiophene, dibenzothiophene, or a combination thereof. In some examples, the sulfur-containing compound can be optionally substituted with one or more methyl substituents, one or more ethyl substituents, or combinations thereof. For example, the sulfur-containing compound can include thiophene, benzothiophene, or dibenzothiophene, that is mono-, di-, tri-, tetra-, penta-, hexa-, hepta-, octa-, or poly-methylated: mono-, di-, tri-, tetra-, penta-, hexa-, hepta-, octa-, or poly-ethylated; or a combination thereof. In some examples, the sulfur-containing compound can be an inorganic sulfur-containing compound, e.g., sulfuric acid, sulfur dioxide, carbon disulfide, methyl sulfide, carbonyl sulfide, hydrogen sulfide, or combinations thereof. In some examples, the concentration of the sulfur-containing compound in the mixture can be from $10^{-9}$ M to 10 M (e.g., $10^{-9}$ M to $10^{-8}$ M).

The sample can comprise, for example, a hydrocarbon fluid, such as petroleum, natural gas, or combinations thereof. In some examples, the sample can comprise the sulfur-containing compound and a solvent. Examples of solvents include, but are not limited to, alcohols (e.g., methanol, ethanol, n-butanol, isopropanol, n-propanol), carboxylic acids (e.g., acetic acid), hydrocarbons (e.g., benzene, toluene, heptane, hexane), water, or combinations thereof. In some examples, the mixture consists of the sample, the parahydrogen, and the catalyst. In some examples, the methods described herein can be used for detecting a sulfur-containing contaminant in a fuel.

In some examples, a spin order can be transferred from the parahydrogen to the sulfur-containing compound thereby hyperpolarizing the sulfur-containing compound during a temporary association of the parahydrogen, the sulfur-containing compound, and the catalyst. In some examples, the spin order can be transferred spontaneously. In some examples, the spin order can be transferred non-spontaneously.

The methods can further comprise, for example, performing an NMR measurement on the mixture comprising the hyperpolarized sulfur-containing compound to detect the hyperpolarized sulfur-containing compound (e.g., from the hyperpolarized NMR signals). Performing the NMR measurement can, for example, comprise a magnetic field. In some examples, the magnetic field can have a strength of from $1 \times 10^{-7}$ T to 100 T. In some examples, the magnetic field can be the Earth's magnetic field.

In some examples, the temporary association of the parahydrogen, the sulfur-containing compound and the catalyst has terminated before the NMR measurement is performed. The sulfur-containing compound has a chemical identity, and, in some examples, the chemical identity of the sulfur-containing compound before the contacting step is the same as the chemical identity of the sulfur-containing compound in the mixture subjected to the NMR measurement step. In some embodiments, detecting the hyperpolarized sulfur-containing compound can comprise quantifying the amount of the sulfur-containing compound in the sample. The hyperpolarized sulfur-containing compound can have, for example, an NMR signal with a phase that is 180 degrees different than the NMR signal from the mixture.

The details of one or more embodiments are set forth in the description below. Other features, objects, and advantages will be apparent from the description and from the claims and the drawings.

DETAILED DESCRIPTION

Figure 1:
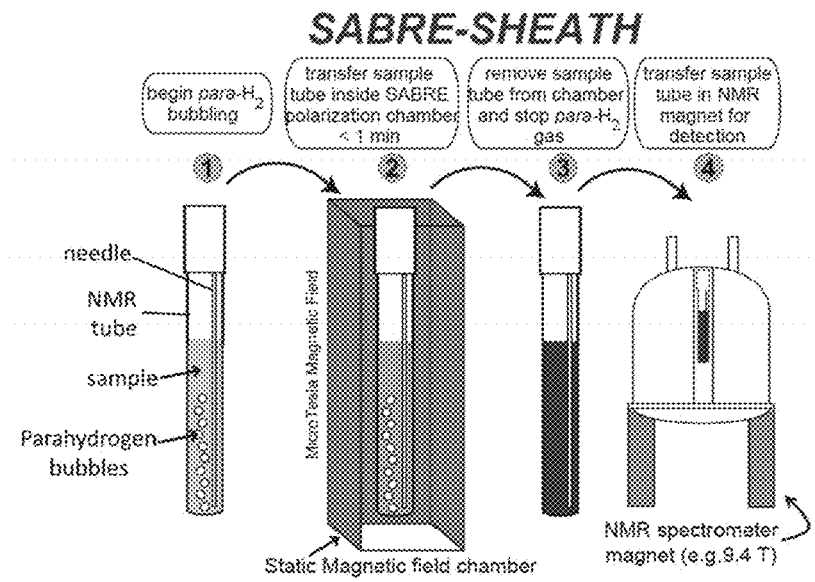
FIG. 1 shows a schematic representation of an exemplary embodiment of the sulfur detection methods.

Sulfur is a common contaminant of crude oil and natural gas. The US EPA regulates sulfur in fuels, and the upper limit has been tightened over the years, with the EPA intending to limit the sulfur level in 2017 down to 10 ppm from the current 30 ppm level. This can require developing better refining solutions for removal of sulfur-containing compounds from fuel. Moreover, it would also be desirable to develop a cost-efficient technology to detect sulfur-containing compounds at a part-per-million (ppm) level in an organic medium with chemical specificity.

In principle, conventional proton nuclear magnetic resonance (NMR) can fulfill this role, although two challenges exist: (i) the detection sensitivity can require lengthy scan times and access to costly high-field NMR equipment, (ii) the background signal can be too strong to delineate these sulfur-containing compounds (at ppm level) vs. hydrocarbons (>90% content). NMR involves the detection of the transitions of nuclear spins between an excited state and a ground state in a magnetic field. The relative weakness of NMR signals exhibited by nuclei with a nonzero magnetic moment results from the way the original energy levels split in a magnetic field (e.g., the Zeeman Effect). The bulk magnetic moment for an ensemble of such nuclei is determined by the Boltzmann population of each energy level. In general, the difference in the energy between these levels is so small that almost-equal spin populations exist across them. For example, in a magnetic field of 9.4 T, such as that found in routine high-resolution NMR spectrometers, the difference in spin population will only be around 1 in 32,000 for $^1$H. Proton ($^1$H) nuclei are the most sensitive, and, for $^{19}$F, $^{31}$P, $^{13}$C, and $^{15}$N, the next most common nuclei to be studied, the sensitivity problem is even more acute, with the associated signal decreasing by factors of 1.2, 15, 64, and $10^4$, respectively. The problem is further exacerbated when the natural abundance of $^{13}$C (1.108%) and $^{15}$N (0.37%) isotopes are taken into account, meaning the effective differences in sensitivity scale from 1 in 32,000 for $^1$H to 1 in 120 million and 1 in 8.7 billion in these nuclei, respectively. (Adams R W et al. *Science* 2009, 323, 1708-1711).

The strength of detectable NMR signals can be enhanced by hyperpolarizing the magnetic nuclei. Hyperpolarization, as used herein, refers to a process in which an excess of magnetic nuclear polarization is induced. This can result in a large increase in available signal due to the much larger inequality of populations across the energy levels. NMR signal amplification by reversible exchange (NMR-SABRE) is a hyperpolarization technology that can increase NMR detection sensitivity, for example, by several orders of magnitude (e.g., 3-6 orders of magnitude). Herein, methods of detecting sulfur-containing compounds in samples are described, for example using NMR-SABRE hyperpolarization of the sulfur-containing compounds in the samples.

Chemical Definitions

Terms used herein will have their customary meaning in the art unless specified otherwise. The organic moieties mentioned when defining variable positions within the general formulae described herein (e.g., the term "halogen") are collective terms for the individual substituents encompassed by the organic moiety. The prefix $C_n$-$C_m$ preceding a group or moiety indicates, in each case, the possible number of carbon atoms in the group or moiety that follows.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, heteroatoms present in a compound or moiety, such as nitrogen, can have hydrogen substituents and/or any permissible substituents of organic compounds described herein which satisfy the valency of the heteroatom. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound (e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

As used herein, the term "alkyl" refers to saturated, straight-chained or branched saturated hydrocarbon moieties. Unless otherwise specified, $C_1$-$C_{50}$ (e.g., $C_1$-$C_{45}$, $C_1$-$C_{40}$, $C_1$-$C_{35}$, $C_1$-$C_{30}$, $C_1$-$C_{25}$, $C_1$-$C_{20}$, $C_1$-$C_{15}$, $C_1$-$C_{16}$, $C_1$-$C_{14}$, $C_1$-$C_{12}$, $C_1$-$C_{10}$, $C_1$-$C_8$, $C_1$-$C_6$, or $C_1$-$C_4$) alkyl groups are intended. Examples of alkyl groups include methyl, ethyl, propyl, 1-methyl-ethyl, butyl, 1-methyl-propyl, 2-methyl-propyl, 1,1-dimethyl-ethyl, pentyl, 1-methyl-butyl, 2-methyl-butyl, 3-methyl-butyl, 2,2-dimethyl-propyl, 1-ethyl-propyl, hexyl, 1,1-dimethyl-propyl, 1,2-dimethyl-propyl, 1-methyl-pentyl, 2-methyl-pentyl, 3-methyl-pentyl, 4-methyl-pentyl, 1,1-dimethyl-butyl, 1,2-dimethyl-butyl, 1,3-dimethyl-butyl, 2,2-dimethyl-butyl, 2,3-dimethyl-butyl, 3,3-dimethyl-butyl, 1-ethyl-butyl, 2-ethyl-butyl, 1,1,2-trimethyl-propyl, 1,2,2-trimethyl-propyl, 1-ethyl-1-methyl-propyl, and 1-ethyl-2-methyl-propyl. Alkyl substituents may be unsubstituted or substituted with one or more chemical moieties. The alkyl group can be substituted with one or more groups including, but not limited to, hydroxyl, halogen, acyl, alkyl, alkoxy, alkenyl, alkynyl, aryl, heteroaryl, aldehyde, amino, cyano, carboxylic acid, ester, ether, ketone, nitro, phosphonyl, silyl, sulfo-oxo, sulfonyl, sulfone, sulfoxide, or thiol, as described below, provided that the substituents are sterically compatible and the rules of chemical bonding and strain energy are satisfied.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halides (halogens; e.g., fluorine, chlorine, bromine, or iodine). The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

As used herein, the term "alkenyl" refers to unsaturated, straight-chained, or branched hydrocarbon moieties containing a double bond. Unless otherwise specified, $C_2$-$C_{50}$ (e.g., $C_2$-$C_{45}$, $C_2$-$C_{40}$, $C_2$-$C_{35}$, $C_2$-$C_{30}$, $C_2$-$C_{25}$, $C_2$-$C_{20}$, $C_2$-$C_{18}$, $C_2$-$C_{16}$, $C_2$-$C_{14}$, $C_2$-$C_{12}$, $C_2$-$C_{10}$, $C_2$-$C_8$, $C_2$-$C_6$, or $C_2$-$C_4$) alkenyl groups are intended. Alkenyl groups may contain more than one unsaturated bond. Examples include ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, and 1-ethyl-2-methyl-2-propenyl. The term "vinyl" refers to a group having the structure —CH=CH$_2$; 1-propenyl refers to a group with the structure -CH=CH—CH$_3$; and 2-propenyl refers to a group with the structure —CH$_2$—CH=CH$_2$. Asymmetric structures such as $(Z^1Z^2)C=C(Z^3Z^4)$ are intended to include both the E and Z isomers. This can be presumed in structural formulae herein wherein an asymmetric alkene is present, or it can be explicitly indicated by the bond symbol C=C. Alkenyl substituents may be unsubstituted or substituted with one or more chemical moieties. Examples of suitable substituents include, for example, alkyl, alkoxy, alkenyl, alkynyl, aryl, heteroaryl, acyl, aldehyde, amino, cyano, carboxylic acid, ester, ether, halide, hydroxyl, ketone, nitro, phosphonyl, silyl, sulfo-oxo, sulfonyl, sulfone, sulfoxide, or thiol, as described below, provided that the substituents are sterically compatible and the rules of chemical bonding and strain energy are satisfied.

As used herein, the term "alkynyl" represents straight-chained or branched hydrocarbon moieties containing a triple bond. Unless otherwise specified, $C_2$-$C_{50}$ (e.g., $C_2$-$C_{45}$, $C_2$-$C_{40}$, $C_2$-$C_{35}$, $C_2$-$C_{30}$, $C_2$-$C_{25}$, $C_2$-$C_{20}$, $C_2$-$C_{18}$, $C_2$-$C_{16}$, $C_2$-$C_{14}$, $C_2$-$C_{12}$, $C_2$-$C_{10}$, $C_2$-$C_8$, $C_2$-$C_6$, or $C_2$-$C_4$) alkynyl groups are intended. Alkynyl groups may contain more than one unsaturated bond. Examples include $C_2$-$C_6$-alkynyl, such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, and 1-ethyl-1-methyl-2-propynyl. Alkynyl substituents may be unsubstituted or substituted with one or more chemical moieties. Examples of suitable substituents include, for example, alkyl, alkoxy, alkenyl, alkynyl, aryl, heteroaryl, acyl, aldehyde, amino, cyano, carboxylic acid, ester, ether, halide, hydroxyl, ketone, nitro, phosphonyl, silyl, sulfo-oxo, sulfonyl, sulfone, sulfoxide, or thiol, as described below.

As used herein, the term "aryl," as well as derivative terms such as aryloxy, refers to groups that include a monovalent aromatic carbocyclic group of from 3 to 50 carbon atoms. Aryl groups can include a single ring or multiple condensed rings. In some embodiments, aryl groups include $C_6$-$C_{10}$ aryl groups. Examples of aryl groups include, but are not limited to, phenyl, biphenyl, naphthyl, tetrahydronaphtyl, phenylcyclopropyl, and indanyl. In some embodiments, the aryl group can be a phenyl, indanyl or naphthyl group. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl substituents may be unsubstituted or substituted with one or more chemical moieties. Examples of suitable substituents include, for example, alkyl, alkoxy, alkenyl, alkynyl, aryl, heteroaryl, acyl, aldehyde, amino, cyano, carboxylic acid, ester, ether, halide, hydroxyl, ketone, nitro, phosphonyl, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, acyl, aldehyde, amino, cyano, carboxylic acid, ester, ether, halide, hydroxyl, ketone, nitro, phosphonyl, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, acyl, aldehyde, amino, cyano, carboxylic acid, ester, ether, halide, hydroxyl, ketone, nitro, phosphonyl, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "acyl" as used herein is represented by the formula —C(O)Z$^1$ where Z$^1$ can be a hydrogen, hydroxyl, alkoxy, alkyl, alkenyl, alkynyl, aryl, heteroaryl, cycloalkyl, cycloalkenyl, heterocycloalkyl, or heterocycloalkenyl group described above. As used herein, the term "acyl" can be used interchangeably with "carbonyl." Throughout this specification "C(O)" or "CO" is a short hand notation for C=O.

The term "acetal" as used herein is represented by the formula $(Z^1Z^2)C(=OZ^3)(=OZ^4)$, where $Z^1$, $Z^2$, $Z^3$ and $Z^4$ can be, independently, a hydrogen, halogen, hydroxyl, alkyl, alkenyl, alkynyl, aryl, heteroaryl, cycloalkyl, cycloalkenyl, heterocycloalkyl, or heterocycloalkenyl group described above.

As used herein, the term "alkoxy" refers to a group of the formula $Z^1$—O—, where $Z^1$ is unsubstituted or substituted alkyl as defined above. Unless otherwise specified, alkoxy groups wherein $Z^1$ is a $C_1$-$C_{50}$ (e.g., $C_1$-$C_{45}$, $C_1$-$C_{40}$, $C_1$-$C_{35}$, $C_1$-$C_{30}$, $C_1$-$C_{25}$, $C_1$-$C_{20}$, $C_1$-$C_{18}$, $C_1$-$C_{16}$, $C_1$-$C_{14}$, $C_1$-$C_{12}$, $C_1$-$C_{10}$, $C_1$-$C_8$, $C_1$-$C_6$, $C_1$-$C_4$) alkyl group are intended. Examples include methoxy, ethoxy, propoxy, 1-methyl-ethoxy, butoxy, 1-methyl-propoxy, 2-methyl-propoxy, 1,1-dimethyl-ethoxy, pentoxy, 1-methyl-butyloxy, 2-methyl-butoxy, 3-methyl-butoxy, 2,2-di-methyl-propoxy, 1-ethyl-propoxy, hexoxy, 1,1-dimethyl-propoxy, 1,2-dimethyl-propoxy, 1-methyl-pentoxy, 2-methyl-pentoxy, 3-methyl-pentoxy, 4-methyl-pentoxy, 1,1-dimethyl-butoxy, 1,2-dimethyl-butoxy, 1,3-dimethyl-butoxy, 2,2-dimethyl-butoxy, 2,3-dimethyl-butoxy, 3,3-dimethyl-butoxy, 1-ethyl-butoxy, 2-ethylbutoxy, 1,1,2-trimethyl-propoxy, 1,2,2-trimethyl-propoxy, 1-ethyl-1-methyl-propoxy, and 1-ethyl-2-methyl-propoxy.

The term "aldehyde" as used herein is represented by the formula —C(O)H.

The terms "amine" or "amino" as used herein are represented by the formula —$NZ^1Z^2$, where $Z^1$ and $Z^2$ can each be substitution group as described herein, such as hydrogen, an alkyl, alkenyl, alkynyl, aryl, heteroaryl, cycloalkyl, cycloalkenyl, heterocycloalkyl, or heterocycloalkenyl group described above.

The terms "amide" or "amido" as used herein are represented by the formula —C(O)$NZ^1Z^2$, where $Z^1$ and $Z^2$ can each be substitution group as described herein, such as hydrogen, an alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" or "carboxyl" group as used herein is represented by the formula —C(O)O⁻.

The term "cyano" as used herein is represented by the formula —CN.

The term "ester" as used herein is represented by the formula —OC(O)$Z^1$ or —C(O)O$Z^1$, where $Z^1$ can be an alkyl, alkenyl, alkynyl, aryl, heteroaryl, cycloalkyl, cycloalkenyl, heterocycloalkyl, or heterocycloalkenyl group described above.

The term "ether" as used herein is represented by the formula $Z^1$O$Z^2$, where $Z^1$ and $Z^2$ can be, independently, an alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $Z^1$C(O)$Z^2$, where $Z^1$ and $Z^2$ can be, independently, an alkyl, alkenyl, alkynyl, aryl, heteroaryl, cycloalkyl, cycloalkenyl, heterocycloalkyl, or heterocycloalkenyl group described above.

The term "halide" or "halogen" or "halo" as used herein refers to fluorine, chlorine, bromine, and iodine.

The term "hydroxyl" as used herein is represented by the formula —OH.

The term "nitro" as used herein is represented by the formula —$NO_2$.

The term "phosphonyl" is used herein to refer to the phospho-oxo group represented by the formula —P(O)(O$Z^1$)$_2$, where $Z^1$ can be hydrogen, an alkyl, alkenyl, alkynyl, aryl, heteroaryl, cycloalkyl, cycloalkenyl, heterocycloalkyl, or heterocycloalkenyl group described above.

The term "silyl" as used herein is represented by the formula —Si$Z^1Z^2Z^3$, where $Z^1$, $Z^2$, and $Z^3$ can be, independently, hydrogen, alkyl, alkoxy, alkenyl, alkynyl, aryl, heteroaryl, cycloalkyl, cycloalkenyl, heterocycloalkyl, or heterocycloalkenyl group described above.

The term "sulfonyl" or "sulfone" is used herein to refer to the sulfo-oxo group represented by the formula —S(O)$_2Z^1$, where $Z^1$ can be hydrogen, an alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

The term "sulfide" as used herein is comprises the formula —S—.

The term "disulfide" as used herein is represented by the formula $Z^1$S—S$Z^2$, where $Z^1$ and $Z^2$ can be, independently, an alkyl, alkenyl, alkynyl, aryl, heteroaryl, cycloalkyl, cycloalkenyl, heterocycloalkyl, or heterocycloalkenyl group described above.

The term "polysulfide" as used herein refers to a class of chemical compounds comprising chains of sulfur atoms.

The term "sulfoxide" as used herein is represented by the formula $Z^1$S(O)$Z^2$, where $Z^1$ and $Z^2$ can be, independently, an alkyl, alkenyl, alkynyl, aryl, heteroaryl, cycloalkyl, cycloalkenyl, heterocycloalkyl, or heterocycloalkenyl group described above.

The term "sulfonic acid" as used herein is represented by the formula —S(O)$_2$OH.

The term "sulfinic acid" as used herein is represented by the formula —S(O)OH.

The term "sulfenic acid" as used herein is represented by the formula —SOH.

The term "sulfimide" as used herein is represented by the formula —S=N—.

The term "sulfoximide" as used herein is represented by the formula —S(O)(=N$Z^1$) where $Z^1$ can be a hydrogen, halogen, hydroxyl, alkyl, alkenyl, alkynyl, aryl, heteroaryl, cycloalkyl, cycloalkenyl, heterocycloalkyl, or heterocycloalkenyl group described above.

The term "sulfonediimine" as used herein is represented by the formula $Z^1$S(=N$Z^2$)(=N$Z^1$)$Z^4$, where $Z^1$, $Z^2$, $Z^3$, and $Z^4$ can, independently, be a hydrogen, halogen, hydroxyl, alkyl, alkenyl, alkynyl, aryl, heteroaryl, cycloalkyl, cycloalkenyl, heterocycloalkyl, or heterocycloalkenyl group described above.

The term "thiol" as used herein is represented by the formula —SH.

The term "thioacetal" as used herein is represented by the formula ($Z^1Z^2$)C(=S$Z^3$)(=O$Z^4$), where $Z^1$, $Z^2$, $Z^3$, and $Z^4$ can be, independently, a hydrogen, halogen, hydroxyl, alkyl, alkenyl, alkynyl, aryl, heteroaryl, cycloalkyl, cycloalkenyl, heterocycloalkyl, or heterocycloalkenyl group described above.

The term "thioaldehyde" or "thial" as used herein is represented by the formula —C(S)H.

The term "thiocarboxylic acid" as used herein is represented by the formula —C(O)SH.

The term "dithiocarboxylic acid" as used herein is represented by the formula —C(S)SH.

The term "thiocyanate" as used herein is represented by the formula —S—CN.

The term "isothiocyanate" as used herein is represented by the formula —N=C=S.

The term "thioester" as used herein is represented by the formula —OC(O)$Z^1$ or —C(O)S$Z^1$, where $Z^1$ can be an alkyl, alkenyl, alkynyl, aryl, heteroaryl, cycloalkyl, cycloalkenyl, heterocycloalkyl, or heterocycloalkenyl group described above.

The term "thioether" as used herein is represented by the formula $Z^1SZ^2$, where $Z^1$ and $Z^2$ can be, independently, an alkyl, alkenyl, alkynyl, aryl, heteroaryl, cycloalkyl, cycloalkenyl, heterocycloalkyl, or heterocycloalkenyl group described above.

The term "thioketal" as used herein is represented by the formula $(Z^1Z^2)C(=SZ^3)(=SZ^4)$, where $Z^1$, $Z^2$, $Z^3$, and $Z^4$ can be, independently, a hydrogen, halogen, hydroxyl, alkyl, alkenyl, alkynyl, aryl, heteroaryl, cycloalkyl, cycloalkenyl, heterocycloalkyl, or heterocycloalkenyl group described above.

The term "thioketone" as used herein is represented by the formula $Z^1C(S)Z^2$, where $Z^1$ and $Z^2$ can be, independently, an alkyl, alkenyl, alkynyl, aryl, heteroaryl, cycloalkyl, cycloalkenyl, heterocycloalkyl, or heterocycloalkenyl group described above.

The term "thiosulfinate" as used herein is represented by the formula $Z^1S(O)SZ^2$, where $Z^1$ and $Z^2$ can be, independently, a hydrogen, halogen, hydroxyl, alkyl, alkenyl, alkynyl, aryl, heteroaryl, cycloalkyl, cycloalkenyl, heterocycloalkyl, or heterocycloalkenyl group described above.

The term "S-nitrosothiol" as used herein is represented by the formula —S—N=O.

The term "S-oxide" or "sulfine" as used herein is represented by the formula —C=S=O.

The term "S,S-dioxide" or "sulfene" as used herein is represented by the formula —C=SO$_2$.

As used herein, Me refers to a methyl group: OMe refers to a methoxy group; and i-Pr refers to an isopropyl group.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible stereoisomer or mixture of stereoisomer (e.g., each enantiomer, each diastereomer, each meso compound, a racemic mixture, or scalemic mixture).

Methods of Detecting Sulfur-Containing Compounds

Described herein are methods of detecting a sulfur-containing compound in a sample. The methods can comprise, for example, contacting a sample comprising a sulfur-containing compound with parahydrogen and a catalyst to form a mixture. The sulfur-containing compound can comprise, for example, an organosulfur compound. Examples of organosulfur compounds include, but are not limited to, thioethers, thioesters, thioacetals, thioketals, thiols, disulfides, polysulfides, sulfoxides, sulfones, thiosulfinates, sulfimides, sulfoximines, sulfonediimines, S-nitrosothiols, sulfur halides, thioketones, thioaldehydes, S-oxides, S,S-dioxides, thiocarboxylic acids, dithiocarboxylic acids, sulfonic acids, sulfinic acids, sulfenic acids, isothiocyanates, thiocyanates, and combinations thereof. In some examples, the organosulfur compound can comprise a sulfur-containing heterocycle. Examples of sulfur-containing heterocycles include, but are not limited to, asphaltenes, benzothiadiazines, benzoxathioles, dibenzothiepines, dithianes, dithietanes, dithiolanes, dithioles, isothiazoles, oxathiolanes, thiadiazoles, thianthrenes, thiazepines, thiazines, thiazoles, thiazolidines, thiazolines, thiazolopyrimidines, thienobenzodiazepines, thienopyridines, thiepines, thiiranes, thiochromanes, thiolactones, thiolanes, thiomorpholines, thiophenes, thioxanthenes, and combinations thereof.

In some examples, the sulfur-containing compound can be optionally substituted, for example, with one or more methyl substituents, one or more ethyl substituents, or combinations thereof. For example, the sulfur-containing compound can be mono-, di-, tri-, tetra-, penta-, hexa-, hepta-, octa-, or poly-methylated; mono-, di-, tri-, tetra-, penta-, hexa-, hepta-, octa-, or poly-ethylated; or a combination thereof.

In some examples, the sulfur-containing heterocycle can comprise a thiophene compound. In some examples, the thiophene compound can comprise thiophene, benzothiophene, dibenzothiophene, or combinations thereof, any of which can be optionally substituted, for example, with one or more methyl substituents, one or more ethyl substituents, or combinations thereof. For example, the sulfur-containing compound can include thiophene, benzothiophene, or dibenzothiophene, that is mono-, di-, tri-, tetra-, penta-, hexa-, hepta-, octa-, or poly-methylated: mono-, di-, tri-, tetra-, penta-, hexa-, hepta-, octa-, or poly-ethylated; or a combination thereof.

In some examples, the sulfur-containing compound can comprise an inorganic sulfur-containing compound. For example, the sulfur-containing compound can include sulfuric acid, sulfur dioxide, carbon disulfide, methyl sulfide, carbonyl sulfide, hydrogen sulfide, or combinations thereof.

In some examples, the concentration of the sulfur-containing compound in the mixture can be $1 \times 10^{-9}$ molar (M) or more (e.g., $2.5 \times 10^{-9}$ M or more, $5 \times 10^{-9}$ M or more, $7.5 \times 10^{-9}$ M or more, $1 \times 10^{-8}$ M or more, $2.5 \times 10^{-8}$ M or more, $5 \times 10^{-8}$ M or more, $7.5 \times 10^{-8}$ M or more, $1 \times 10^{-7}$ M or more, $2.5 \times 10^{-7}$ M or more, $5 \times 10^{-7}$ M or more, $7.5 \times 10^{-7}$ M or more, $1 \times 10^{-6}$ M or more, $2.5 \times 10^{-6}$ M or more, $5 \times 10^{-6}$ M or more, $7.5 \times 10^{-6}$ M or more, $1 \times 10^{-5}$ M or more, $2.5 \times 10^{-5}$ M or more, $5 \times 10^{-5}$ M or more, $7.5 \times 10^{-5}$ M or more, $1 \times 10^{-4}$ M or more, $2.5 \times 10^{-4}$ M or more, $5 \times 10^{-4}$ M or more, $7.5 \times 10^{-4}$ M or more, $1 \times 10^{-3}$ M or more, $2.5 \times 10^{-3}$ M or more, $5 \times 10^{-3}$ M or more, $7.5 \times 10^{-3}$ M or more, $1 \times 10^{-2}$ M or more, $2.5 \times 10^{-2}$ M or more, $5 \times 10^{-2}$ M or more, $7.5 \times 10^{-2}$ M or more, $1 \times 10^{-1}$ M or more, $2.5 \times 10^{-1}$ M or more, $5 \times 10^{-1}$ M or more, $7.5 \times 10^{-1}$ M or more, or 1 M or more).

In some examples, the concentration of the sulfur-containing compound in the mixture can be 10 M or less (e.g., 7.5 M or less, 5 M or less, 2.5 M or less, 1 M or less, $7.5 \times 10^{-1}$ M or less, $5 \times 10^{-1}$ M or less, $2.5 \times 10^{-1}$ M or less, $1 \times 10^{-1}$ M or less, $7.5 \times 10^{-2}$ M or less, $5 \times 10^{-2}$ M or less, $2.5 \times 10^{-2}$ M or less, $1 \times 10^{-2}$ M or less, $7.5 \times 10^{-2}$ M or less, $5 \times 10^{-3}$ M or less, $2.5 \times 10^{-3}$ M or less, $1 \times 10^{-3}$ M or less, $7.5 \times 10^{-4}$ M or less, $5 \times 10^{-4}$ M or less, $2.5 \times 10^{-4}$ M or less, $1 \times 10^{-4}$ M or less, $7.5 \times 10^{-5}$ M or less, $5 \times 10^{-5}$ M or less, $2.5 \times 10^{-5}$ M or less, $1 \times 10^{-5}$ M or less, $7.5 \times 10^{-6}$ M or less, $5 \times 10^{-6}$ M or less, $2.5 \times 10^{-6}$ M or less, $1 \times 10^{-6}$ M or less, $7.5 \times 10^{-7}$ M or less, $5 \times 10^{-7}$ M or less, $2.5 \times 10^{-7}$ M or less, $1 \times 10^{-7}$ M or less, $7.5 \times 10^{-8}$ M or less, $5 \times 10^{-8}$ M or less, $2.5 \times 10^{-8}$ M or less, $1 \times 10^{-8}$ M or less, $7.5 \times 10^{-9}$ M or less, $5 \times 10^{-9}$ M or less, or $2.5 \times 10^{-9}$ M or less).

The concentration of the sulfur-containing compound in the mixture can range from any of the minimum values described above to any of the maximum values described above. For example, the concentration of the sulfur-containing compound in the mixture can be from $1\times10^{-9}$ M to 10 M (e.g., from $1\times10^{-9}$ M to $1\times10^{-5}$ M, from $1\times10^{-5}$ M to 10 M, from $1\times10^{-9}$ M to $1\times10^{-6}$ M, from $1\times10^{-6}$ M to $1\times10^{-3}$ M, from $1\times10^{-3}$ M to 1 M, or from $1\times10^{-9}$ M to $1\times10^{-8}$ M).

Dihydrogen exists in various spin states, in which the spins of the individual nuclei are either aligned (ortho, the higher energy state), or opposed (para, the lower energy spin state). Parahydrogen (p-$H_2$) is a nuclear spin state isomer of dihydrogen with the spin configuration $\alpha\beta$-$\beta\alpha$. Parahydrogen has no net magnetic moment and is therefore unobservable in this form by magnetic resonance methods. The binuclear spin systems of dihydrogen, comprising 75% ortho and 25% para forms, can be hyperpolarized (e.g., shifting the equilibrium to the para form) simply by cooling to low temperature in the presence of a suitable conversion catalyst, which promotes conversion to the lower energy parahydrogen state. In this process, the role of the conversion catalyst is to perturb the dihydrogen molecule and thereby reduce its symmetry; otherwise a quantum mechanical selection rule prevents interconversion between the two spin states. Once separated from the conversion catalyst and returned to room temperature, the parahydrogen spin state can last for over a year (in the absence of external effects). Parahydrogen is relatively inexpensive to prepare and can be arranged at different types of catalysts. In some examples, parahydrogen can serve as a source of NMR hyperpolarization.

The catalyst can comprise a homogeneous or heterogeneous polarization transfer catalyst. In some examples, the catalyst can comprise a metal complex, such as a transition metal complex. Metal complexes, such as transition metal complexes, can allow the attachment of parahydrogen and numerous different sulfur-containing compounds, such as by coordination bonding. Examples of transition metals include, but are not limited to, Ru, Rh, Ir, W, Pd, and Pt. In some examples, the catalyst can comprise an iridium complex.

The sample can comprise any sample of interest. In some examples, the sample can comprise a hydrocarbon fluid, such as petroleum, natural gas, or combinations thereof. In some examples, the sample can comprise the sulfur-containing compound and a solvent. Examples of solvents include, but are not limited to, alcohols (e.g., methanol, ethanol, n-butanol, isopropanol, n-propanol), carboxylic acids (e.g., acetic acid), hydrocarbons (e.g., benzene, toluene, heptane, hexane), water, and combinations thereof. In some examples, the methods described herein can be used for detecting a sulfur-containing contaminant in a fuel (e.g., crude oil, crude natural gas, the refined products thereof, or combinations thereof). In some examples, the mixture consists of the sample (including the sulfur-containing compound), parahydrogen, and the catalyst.

In some examples, a spin order can be transferred from the parahydrogen to the sulfur-containing compound thereby hyperpolarizing the sulfur-containing compound during a temporary association of the parahydrogen, the sulfur-containing compound, and the catalyst. The catalyst can act as a broker between the parahydrogen and the sulfur-containing compound. The temporary association of the parahydrogen, the sulfur-containing compound, and the catalyst can, for example, comprise a temporary binding (or bonding) of the parahydrogen and the sulfur-containing compound to the catalyst. Temporarily binding the parahydrogen to the catalyst allows the polarization of the parahydrogen to become transferrable.

Further, when both the parahydrogen and the sulfur-containing compound are temporarily associated with the catalyst (e.g., temporarily bound to the catalyst), the catalyst can mediate a coupling of the nuclear spins of the parahydrogen and the sulfur-containing compound. By mediating the coupling, the sulfur-containing compound becomes a possible destination for the polarization of the parahydrogen to be transferred to. In other words, the temporary association of the parahydrogen, the sulfur-containing compound, and that catalyst allows the spin order of the parahydrogen to be transferred to the sulfur-containing compound, thereby hyperpolarizing the sulfur-containing compound.

The spin order can, for example, be transferred spontaneously. As used herein, a spontaneous spin order transfer means that the spin order is transferred without applying a radio-frequency field and/or radio-frequency pulse. In some examples, the spin order can be transferred non-spontaneously. A used herein, a non-spontaneous spin order transfer means that the spin order is transferred by exposing the mixture to radio-frequency fields and/or radio-frequency pulses. In some examples, the spin-order transfer can be enhanced by agitating the mixture (e.g., by shaking the mixture). In some examples, the spin-order transfer can be enhanced by a static magnetic field.

In some examples, the methods can further comprise performing a measurement on the mixture comprising the hyperpolarized sulfur-containing compound to detect the hyperpolarized sulfur-containing compound. The measurement can, for example, comprise a magnetic resonance measurement, such as Nuclear Magnetic Resonance (NMR) spectroscopy, Magnetic Resonance Imaging (MRI), or combinations thereof. In some examples, detecting the sulfur-containing compound can comprise detecting the structural signature of the sulfur-containing compound in the measurement.

In some examples, the methods can comprise performing an NMR measurement on the mixture comprising the hyperpolarized sulfur-containing compound to detect the hyperpolarized sulfur-containing compound (e.g., from the hyperpolarized NMR signals). In some examples, detecting the sulfur-containing compound can comprise detecting the structural signals of the sulfur-containing compound in the NMR measurement. The sulfur-containing compound can be present in an amount in the sample and, for example, detecting the hyperpolarized sulfur-containing compound can comprise quantifying the amount of the sulfur-containing compound in the sample.

In some examples, the temporary association of the parahydrogen, the sulfur-containing compound and the catalyst has terminated before the NMR measurement is performed. There is no net chemical reaction necessary between the parahydrogen and the sulfur-containing compound in order to achieve the spin order transfer. In other words, the sulfur-containing compound has a chemical identity, and, in some examples, the chemical identity of the sulfur-containing compound before the contacting step is the same as the chemical identity of the sulfur-containing compound in the mixture subjected to the NMR measurement step.

In some examples, performing the NMR measurement can comprise a magnetic field. The magnetic field can, for example, have a strength of $1\times10^{-7}$ Tesla (T) or more (e.g., $2.5\times10^{-7}$ T or more, $5\times10^{-7}$ T or more, $7.5\times10^{-7}$ T or more, $1\times10^{-6}$ T or more, $2.5\times10^{-6}$ T or more, $5\times10^{-6}$ T or more, $7.5\times10^{-6}$ T or more, $1\times10^{-5}$ T or more, $2.5\times10^{-5}$ T or more, $5\times10^{-5}$ T or more, $7.5\times10^{-5}$ T or more, $1\times10^{-4}$ T or more, $2.5 \times 10^{-4}$ T or more, $5 \times 10^{-4}$ T or more, $7.5 \times 10^{-4}$ T or more, $1 \times 10^{-3}$ T or more, $2.5 \times 10^{-3}$ T or more, $5 \times 10^{-3}$ T or more, $7.5 \times 10^{-3}$ T or more, $1 \times 10^{-2}$ T or more, $2.5 \times 10^{-2}$ T or more, $5 \times 10^{-2}$ T or more, $7.5 \times 10^{-2}$ T or more, $1 \times 10^{-1}$ T or more, $2.5 \times 10^{-1}$ T or more, $5 \times 10^{-1}$ T ore, $7.5 \times 10^{-1}$ T or more, 1 T or more, 2.5 T or more, 5 T or more, 7.5 T or more, or 10 T or more).

In some examples, the magnetic field can have a strength of 100 T or less (e.g., 75 T or less, 50 T or less, 25 T or less, 10 T or less, 7.5 T or less, 5 T or less, 2.5 T or less, 1 T or less, $7.5 \times 10^{-1}$ T or less, $5 \times 10^{-1}$ T or less, $2.5 \times 10^{-1}$ T or less, $1 \times 10^{-1}$ T or less, $7.5 \times 10^{-2}$ T or less, $5 \times 10^{-2}$ T or less, $2.5 \times 10^{-2}$ T or less, $1 \times 10^{-2}$ T or less, $7.5 \times 10^{-3}$ T or less, $5 \times 10^{-3}$ T or less, $2.5 \times 10^{-3}$ T or less, $1 \times 10^{-3}$ T or less, $7.5 \times 10^{-4}$ T or less, $5 \times 10^{-4}$ T or less, $2.5 \times 10^{-4}$ T or less, $1 \times 10^{-4}$ T or less, $7.5 \times 10^{-5}$ T or less, $5 \times 10^{-5}$ T or less, $2.5 \times 10^{-5}$ T or less, $1 \times 10^{-5}$ T or less, $7.5 \times 10^{-6}$ T or less, $5 \times 10^{-6}$ T or less, $2.5 \times 10^{-6}$ T or less, or $1 \times 10^{-6}$ T or less).

The strength of the magnetic field can range from any of the minimum values described Above to any of the maximum values described above. For example, the magnetic field can have a strength of from $1 \times 10^{-7}$ t to 100 t (e.g., From $1 \times 10^{-7}$ t to $1 \times 10^{-3}$ t, from $1 \times 10^{-3}$ t to 100 T. From $1 \times 10^{-7}$ t to $1 \times 10^{-6}$ t, from $1 \times 10^{-6}$ t to $1 \times 10^{-5}$ t, from $1 \times 10^{-5}$ t to $1 \times 10^{-4}$ t, from $1 \times 10^{-4}$ t, to $1 \times 10^{-3}$ t, from $1 \times 10^{-1}$ t to $1 \times 10^{-2}$ t, from $1 \times 10^{-2}$ t to $1 \times 10^{-1}$ t, from $1 \times 10^{-1}$ t to 1 t, from 1 t to 10 t, from 10 t to 100 t, or from $5 \times 10^{-7}$ t to 50 t). In some embodiments, the magnetic field is an applied magnetic field.

In some examples, the hyperpolarization can allow for the use of low-field NMR (e.g., 1 T) while maintaining detection sensitivity. In some examples, the Earth's magnetic field, which has a strength of from 25 microTesla (μT) to 65 μT (e.g., $2.5 \times 10^{-5}$ T to $6.5 \times 10^{-5}$ T), can be the magnetic field used to perform the NMR measurement (e.g., Earth's field NMR). The use of low-field NMR can allow for a low-cost hardware setup to be used for detection of sulfur-containing compounds for various applications, including, for example, those in petroleum and natural gas industries as well as the refining processes. The use of low-field NMR detection can allow for in-operando detection of industrial scale processes, for example including in-operando reactor imaging and other types of process visualization in space and time.

The hyperpolarized sulfur-containing compound can have, for example, an NMR signal with a phase that is 180 degrees different than a NMR signal from the mixture. This phase difference can allow for the hyperpolarized NMR signals of the sulfur-based compound to be more easily distinguished from any background NMR signal, which can enhance the NMR detection sensitivity and the signal-to-noise ratio for the sulfur-containing compounds.

The examples below are intended to further illustrate certain aspects of the systems and methods described herein, and are not intended to limit the scope of the claims.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of measurement conditions, e.g., component concentrations, temperatures, pressures and other measurement ranges and conditions that can be used to optimize the described process.

Example 1

Described herein are methods and systems for NMR-SABRE hyperpolarization detection of sulfur-containing compounds. In addition to increased detection sensitivity, the phase of the enhanced NMR signal (via SABRE hyperpolarization) is 180 degrees off from the rest of the NMR background signal. As a result, the NMR detection sensitivity is enhanced, and the NMR signatures of the sulfur-containing compounds can be delineated from the background NMR signal (e.g., the non-hyperpolarized signal). Furthermore, the additional benefits of hyperpolarization is the possibility of using low magnetic field NMR (e.g. 1 T) while maintaining enhanced detection sensitivity.

The class of sulfur-containing compounds that was hyperpolarized is a class of compounds that was not previously amenable to NMR signal amplification by reversible exchange (NMR-SABRE) hyperpolarization method. This method can be applied for hyperpolarization of sulfur-containing compounds, and can allow enhancing the detection sensitivity for specific sulfur-containing compounds (e.g., perform analysis in seconds vs. hours with conventional NMR). With regards to detection of sulfur-containing compounds, such aromatic sulfur-based heterocycles, these compounds can potentially be detected in very small quantities and concentrations, and SABRE hyperpolarization can provide an additional signature of reversed phase NMR signal in hyperpolarized S-containing molecules.

Figure 2:
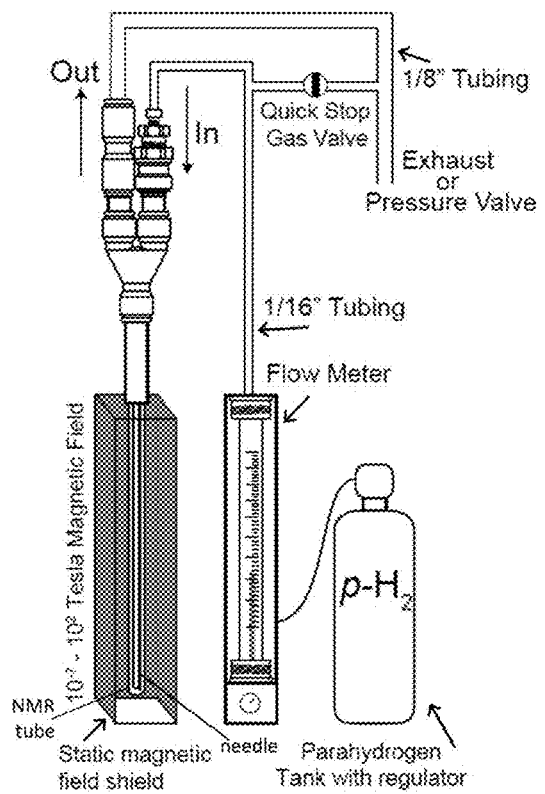
FIG. 2 shows a schematic representation of the parahydrogen contacting the sample.

The method for performing the NMR-SABRE hyperpolarization is shown schematically, for example, in FIG. 1. The sample can be contained within a suitable container, such as an NMR tube (e.g., a 5 mm NMR tube). The catalyst can be added to the sample, for example by adding the catalyst to the NMR tube. The catalyst can be added heterogeneously within the detection volume, or injected into the sample (e.g., via the needle) separately or with the parahydrogen. The parahydrogen can, for example, be contacted with the sample by bubbling the parahydrogen into the sample, such as through a small tube or needle (e.g., the parahydrogen can be infused into the sample). The mixture comprising the sample, the catalyst, and the parahydrogen can then be transferred into a low-magnetic field chamber (e.g., a chamber that can be used for SABRE polarization transfer), where the spin order can be transferred from the parahydrogen to the sulfur-containing compound in the sample. In some examples, the low-magnetic field chamber can comprise a static magnetic field chamber, where a static magnetic field (e.g., with a strength in the microTesla range) can be used to enhance the spin order transfer. The parahydrogen infusion and low-magnetic field chamber are shown in more detail in FIG. 2. As shown in FIG. 2, the parahydrogen can be provided, for example, from a tank through a flow meter and any appropriate tubing, valve(s), regulator(s), or combinations thereof.

Figure 3:
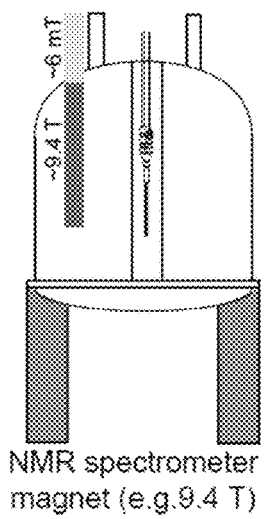
FIG. 3 shows a schematic representation of the NMR detection.

Referring again to FIG. 1, after the spin order transfer, the sample containing the now hyperpolarized sulfur-containing compound can be removed from the low-magnetic field chamber and transferred to a NMR spectrometer for performing the NMR measurement to detect the hyperpolarized sulfur-containing compound. The hyperpolarized sample inside the NMR spectrometer is shown in more detail in FIG. 3. The magnetic field inside the NMR spectrometer can be, for example, 9.4 T, while the magnetic field outside the NMR spectrometer can be ~6 mT.

The general method shown in FIG. 1 can be performed ex situ or in situ. In some examples, the method shown schematically in FIG. 1 can be modified such that the NMR detection can be performed directly in the static magnetic field chamber.

Figure 4:
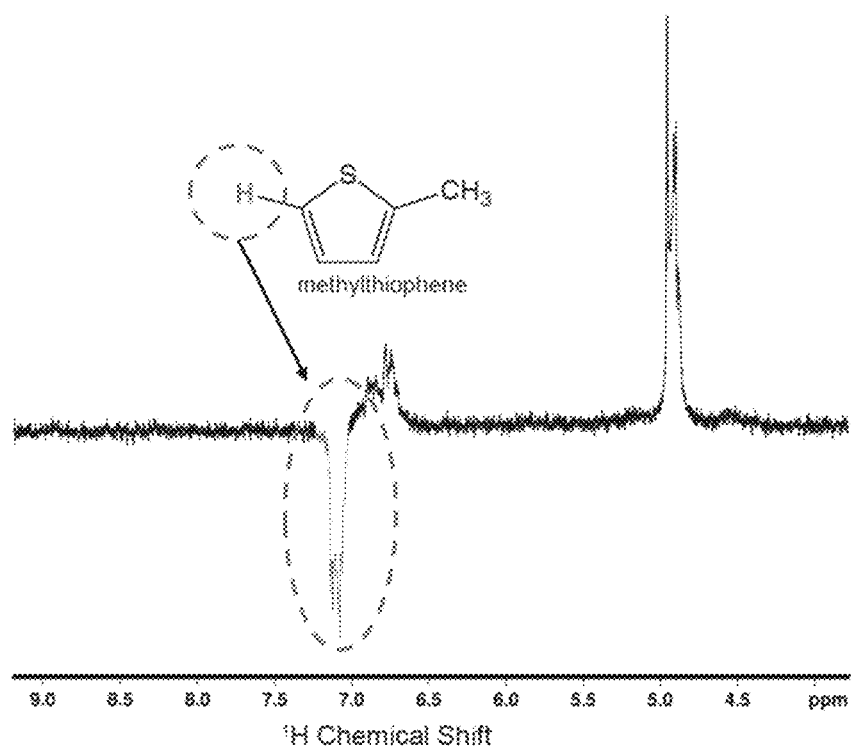
FIG. 4 shows the NMR spectrum detected for hyperpolarized methylthiophene.
Figure 5:
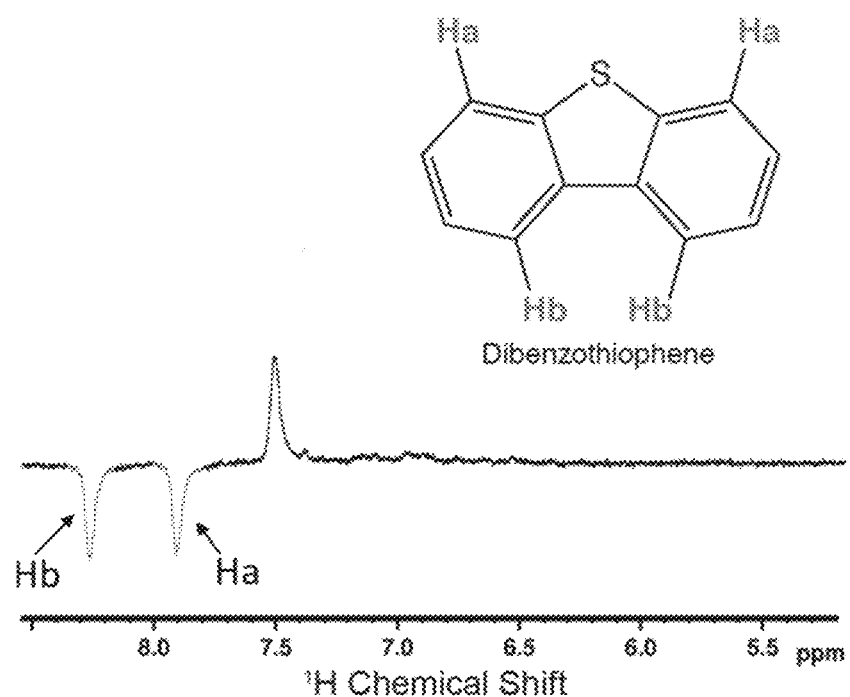
FIG. 5 shows the NMR spectrum detected for hyperpolarized dibenzothiophene.

The set-up shown schematically in FIG. 1 was used to detect samples comprising methylthiophene (FIG. 4) and dibenzothiophene (FIG. 5). The 180° phase difference in the hyperpolarized signals can clearly be seen in the NMR spectra collected using the hyperpolarization method on methylthiophene (FIG. 4) and dibenzothiophene (FIG. 5).

Herein, NMR-SABRE hyperpolarization detection of representative sulfur-containing compounds (e.g., methylthiophene and dibenzothiophene) in organic solvents is described. The methods described herein can enable detection of trace quantities (e.g., parts per million) of sulfur-containing compounds (e.g., thiophene and dibenzothiophene) in organic medium using NMR detection. The methods described herein can be used in conjunction with low-field NMR detection, because NMR signal of hyperpolarized S-containing compounds is not endowed by the NMR magnet and high signal-to-noise ratio (SNR) spectra can be obtained with relatively low field (and low cost) NMR systems (e.g., ~1 T). In addition to increased detection sensitivity, the phase of the enhanced NMR signal (via SABRE hyperpolarization) is 180 degrees off from the rest of the NMR background signal. As a result, the NMR detection sensitivity is enhanced, and the NMR signatures of the sulfur-containing compounds can be delineated from the background NMR signal (e.g., the non-hyperpolarized signal). The methods described herein can be used, for example, as a high-throughput and low-cost method of detection of sulfur-based compounds in petroleum and natural gas and their refined products Example 2

Figure 6:
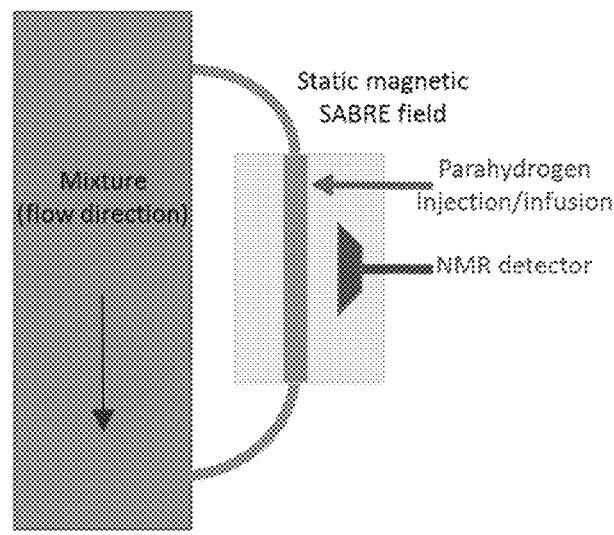
FIG. 6 shows a schematic representation of an exemplary embodiment of the sulfur detection method.

Another example application of the methods described herein is shown schematically in FIG. 6. A "flow through" SABRE hyperpolarization method is shown schematically in FIG. 6. Here, the method can be performed in a continuous flow manner, where a portion of the sample is directed into a continuous flow chamber where the sample is contacted with the catalyst and parahydrogen before flowing through an NMR detector.

Example 3

Figure 7:
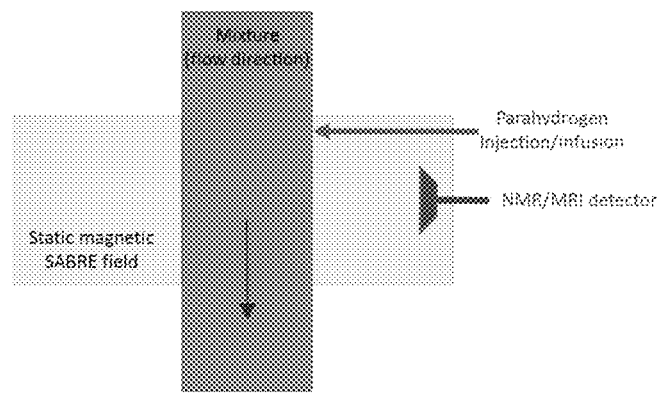
FIG. 7 shows a schematic representation of an exemplary embodiment of the sulfur detection method.

Another example application of the methods described herein is shown schematically in FIG. 7. An in operando SABRE hyperpolarization method is shown schematically in FIG. 7. Here, the method can be performed in a continuous flow manner, where the sample continuously flows through a static magnetic SABRE field chamber where the sample is contacted with the catalyst and parahydrogen before NMR detection is performed.

Example 4

NMR hyperpolarization can increase nuclear spin polarization from equilibrium Boltzmann values of $10^{-6}$-$10^{-5}$ to the order of unity, resulting in concomitant gains in NMR signal and signal-to-noise ratio (SNR) (Nikolaou P et al. Chem. Eur. J. 2015, 21, 3156-3166; Abragam A and Goldman M. Rep. Prog. Phys. 1978, 41, 395-467; Ardenkjaer-Larsen J H et al. Proc. Natl. Acad. Sci. U.S.A 2003, 100, 10158-10163: Goodson B M. J. Magn. Reson. 2002, 155, 157-216; Bowers C R and Weitekamp D P. Phys. Rev. Lett. 1986, 57, 2645-2648). The vast majority of NMR hyperpolarization techniques require sophisticated, expensive, and low-throughput equipment (dubbed hyperpolarizers (Ardenkjaer-Larsen J H et al. Proc. Natl. Acad. Sci. U.S.A 2003, 100, 10158-10163)) for producing atoms or molecules with hyperpolarized (HP) nuclear spins. As a result, the hyperpolarized substances produced in such fashion are generally expensive and time-consuming to create. Despite these limitations, hyperpolarization techniques promise to revolutionize biomedical research because the benefits of gaining new insights into fundamental biomedical questions and development of personalized imaging medicines (e.g., molecular probes that can answer questions specific to the disease stage, as well as genetic and metabolic underpinning) outweigh the cost/throughput issues (Brindle K M. J. Am. Chem. Soc. 2015, 137, 6418-6427; Kurhanewicz J et al. Neoplasia 2011, 13, 81-97; Comment A and Merritt M E. Biochemistry 2014, 53, 7333-7357: Nelson S J et al. Sci. Transl. Med. 2013, 5, 198ra108).

However, the development of NMR Signal Amplification By Reversible Exchange (SABRE) (Adams R W et al. Science 2009, 323, 1708-1711) enables inexpensive, high-throughput hyperpolarization without the need for complex hyperpolarizer devices. As a result, SABRE has the potential to transform structural analysis well beyond biomedical research. Despite being structurally limited to hyperpolarization of N-heterocycles, the SABRE technique has been applied for structural studies (Eshuis N et al. Angew. Chem. Int. Ed. 2015, 54, 1481-1484) of coffee extracts (Hermkens N K J et al. Anal. Chem. 2016, 88, 3406-3412) and biofluids (Reile I et al. Analyst 2016, 141, 4001-4005), in addition to hyperpolarization of contrast agents for biomedical applications (Theis T et al. J. Am. Chem. Soc. 2015, 137, 1404-1407; Shchepin R V et al. ACS Sensors 2016, 1, 640-644; Barskiy D A et al. J. Am. Chem. Soc. ASAP 2016, DOI: 10.1021/acs.jpcc.6b07555: Shchepin R V et al. J. Phys. Chem. Lett. 2015, 6, 1961-1967).

Herein, SABRE of sulfur-containing heterocycles (S-SABRE) is discussed, which enables hyperpolarization of a new class of compounds-paving the way to new applications. In particular, this approach can be useful for sensing S— heterocyclic compounds in petroleum and refined petroleum products, where structural information (typically obtained via elemental analysis, solid-state NMR, or other methods) guides the refining process and ultimately determines the sulfur-removal efficiency (Kelemen S R et al. Energy & Fuels 2007, 21, 1548-1561: Kelemen S R et al. Energy & Fuels 2006, 20, 635-652). Sulfur is a highly unwanted pollutant, and the reduction of its content in fuels (and consequent emission into the atmosphere) continues to be a major effort, as it is necessary to reduce levels in fuels to a few parts per million (ppm) (United States Environment Protection Agency, Office of Transportation and Air Quality. EPA-420-F-14-007, 2014). For example, it is predicted that the additional refining efforts to reach the desired future standards will lead to additional fuel cost increases at the pump of ~6-9 cents per gallon (Coomes J. Bloomberg BNA, Daily Environment Report, Bloomberg, http://wwwv.bna.com/epa-tier-rule-n 17179882576/, 2014).

Here. SABRE is demonstrated with S-heterocycles using two representative examples of substituted thiophenes-sulfur-containing compounds found in petroleum: methylthiophene and dibenzothiophene (Kropp K G and Fedorak P M. Can. *J. Microbiol.* 1998, 44, 605-622). In particular, the latter compound and its methylated derivatives occur widely in heavier petroleum fractions (Ho T C. *Catal. Today* 2004, 98, 3-18).

Dibenzothiphene and 2-methylthiophene stock solutions (I, II, III, IV) were prepared according to the following procedure. Dibenzothiophene (0.092 g, 0.184 g, or 0.369 g) was placed in Scott's Duran 25 mL sample vials with GL25 caps and dissolved in benzene-$d_6$ (10 mL) resulting in 0.050 M (I), 0.100 M (II), and 0.200 M (III) final stock solutions, respectively, 2-Methylthiophene (0.098 g) was placed in Scott's Duran 25 mL sample vials with GL25 caps and dissolved in benzene-$d_6$ (10 mL), resulting in a 0.100 M (IV) solution. The vials were degassed by flushing with Argon/vortexing at least three times for each sample.

The Ir catalyst stock solution (V) was prepared according to the following procedure. Non-activated iridium catalyst ([IrCl(CODXIMes)], prepared as described elsewhere (Theis T et al. *J. Am. Chem. Soc.* 2015, 137, 1404-1407) MW~640, 73.1 mg), was placed in Scott's Duran 25 mL sample vial with GL25 cap and dissolved in methanol-$d_4$ (20 mL), resulting in a final solution (V) of 5.71 mM. The vial was degassed by flushing with Argon/vortexing at least three times.

Figure 8:
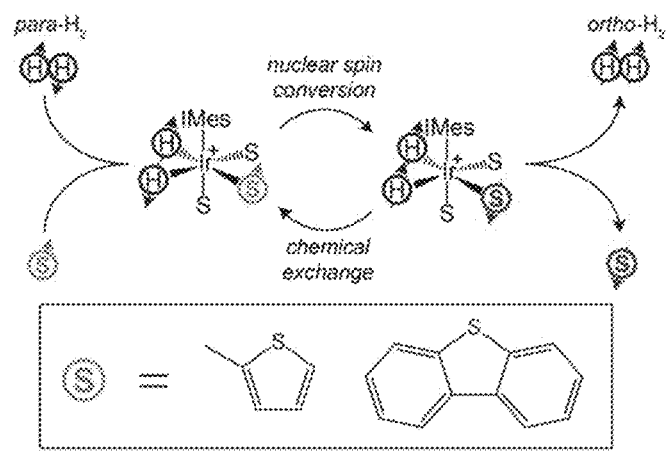
FIG. 8 is a schematic representation of the SABRE hyperpolarization process, which relies on the chemical exchange of the hexacoordinate Ir-IMes catalyst with para-hydrogen and a to-be-hyperpolarized sulfur-containing substrate.
Figure 9:
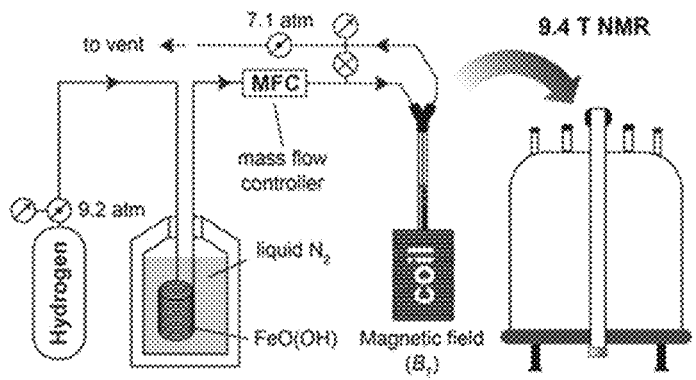
FIG. 9 is a schematic diagram of the experimental setup showing the production of parahydrogen (~50% para-state using a liquid N2 cooling source). Para-hydrogen is controlled using mass flow controller (MFC); Ø is a safety valve (~7.1 atm) employed to regulate $H_2$ pressure in the NMR tube, and @ is a bypass valve to provide rapid cessation of parahydrogen bubbling through the solution in the NMR tube. Following SABRE mixing at BT the sample tube is rapidly transferred to the 9.4 T to permit high-field NMR acquisition.

The activated form of the catalyst previously shown to be the most potent for SABRE of N-heterocycles (Ir-IMes hexacoordinate complex (Cowley M J et al. *J. Am. Chem. Soc.* 2011, 133, 6134-6137)) was employed for chemical exchange with parahydrogen and the to-be-hyperpolarized sulfur-containing substrates (S), FIG. 8. A previously developed high-pressure setup (Truong M L et al. *J. Phys. Chem. B* 2014, 18 13882-13889) was employed with a magnetic field for polarization transfer ($B_T$) provided by a small solenoid (FIG. 9). The latter provided a fine control of $B_T$ vs. a relatively inhomogeneous fringe field of the 9.4 T NMR spectrometer used (Truong M L et al. *J. Phys. Chem. B* 2014, 18 13882-13889).

Stock solutions I, II, III, or IV were mixed with sock solution V in a 3:7 ratio, resulting in mixtures containing 4 mM of Ir catalyst and 15, 30, or 60 mM of dibenzothiophene correspondingly. Freshly prepared mixtures were used within 10 minutes for the best polarization results. Each of the resulting solutions (0.50 mL) was transferred via Ranin XLS pipet into an Argon-filled medium-walled NMR sample tube (5 mm medium wall precision, 3.43 mm ID, 9 in. long. Wilmad glass P/N 503-PS-9) equipped with a Teflon tube extension (0.25 in. OD, 3/16 in. ID), which was approximately 7 cm long. The tube was attached to the setup through a push-to-connect adapter (Truong M L et al. *J. Phys. Chem. B* 2014, 18 13882-13889). The SABRE sample was activated by bubbling parahydrogen (para-$H_2$) at 90 sccm for (~2 min) under ~6 atm para-$H_2$ (50% para-fraction): flow rate was controlled by a mass flow controller (Sierra Instruments, Monterey, Calif., model number C100L-DD-OV1-SV1-PV2-V 1-S0-C0).

$^1$H SABRE hyperpolarization procedure was performed similarly to that described elsewhere (Theis T et al. *J. Am. Chem. Soc.* 2015, 137, 1404-1407). Briefly, the sample tube with activated catalyst and to-be-hyperpolarized substrate was placed in the fringe field of the magnet at 6±4 mT (measured with gauss meter) or left in the Earth's magnetic field (ca. 50 µT). Alternatively, the Earth's magnetic field was attenuated using three-layered mu-metal shield (6 in. ID & 15 in. in length, part number ZG-206, Magnetic Shield Corp., Bensenville, Ill.), which was degaussed before use. The magnetic field in the mT-range was created using a custom-built solenoid coil and a power supply (GPRS series, GW INSTEK). After cessation of para-$H_2$ bubbling the sample was quickly transferred from the shield to the Earth's magnetic field followed by sample insertion in the bore of 9.4 T magnet and acquisition of the $^1$H NMR spectrum. $^1$H peaks integrals were integrated with respect to a sample $^1$H thermal signal the sample. The $^1$H NMR spectrum of dibenzothiophene at thermal equilibrium is the top spectrum of FIG. 10, with the SABRE hyperpolarization spectrum of dibenzothiophene conducted in Earth's magnetic field being the middle spectrum of FIG. 10, and the SABRE hyperpolarization spectrum of dibenzothiophene conducted in the ~11 mT magnetic field being the bottom spectrum of FIG. 10. Additional spectral data for dibenzothiophene are shown in FIG. 11 to FIG. 20.

Simulations were carried out by treating numerically the Liouville-von Neumann equation for spin density matrix according to the algorithm described elsewhere (Pravdivtsev A N et al. *ChemPhysChem* 2013, 14, 3327-3331). The initial density matrix of p-$H_2$ was constructed as $\hat{\rho}_{H_2}=\frac{1}{4}\hat{1}-\hat{I}_1\hat{I}_2$. The density matrix of an active SABRE complex was modeled by 10-spin system and constructed as a direct product between $\hat{\rho}_{H_2}$ and unit matrix representing thermally polarized 8-spin system of a dibenzothiophene. In order to account for averaging of coherences arising from the time dispersion of the polarization build-up process, only diagonal elements of the matrix written on the basis of low-field nuclear spin Hamiltonian were left; all non-diagonal elements vanished. The low-field nuclear spin Hamiltonian was given by NMR parameters of dibenzothiophene (Table 1) as well as by chemical shifts and the spin-spin couplings of hydride nuclei in the complex. The latter quantities were −23 ppm and −7 Hz, respectively. Polarization transfer driving spin-spin coupling constant between one of the hydride nuclei and two $H_A$ protons of the dibenzothiophene was taken as 1 Hz (Eshuis N et al. *J. Magn. Reson.* 2016, 265, 59-66). Then, to describe the spin state of dissociated dibenzothiophene, the density matrix was reduced in its dimensionality by taking trace over the two hydride spin states. Finally, the sample was transferred to the high field where NMR spectrum was detected. This was modeled by solving the Liouville-von Neumann equation for the density matrix with time-dependent Hamiltonian. The linear profile of the magnetic field variation was used. Thus, the density matrix at high magnetic field was obtained, which allows calculating NMR spectrum. Relaxation effects were not included in the simulations.

TABLE 1

NMR chemical shifts (δ) and J-coupling parameters of dibenzothiophene.

|  | A | B | C | D |
|---|---|---|---|---|
| δ (ppm) | 7.53 | 7.12 | 7.16 | 7.84 |
| J (Hz) | A | B | C | D |
| A | — | 7.95 | 1.21 | 0.71 |
| B |  | — | 7.13 | 1.09 |
| C |  |  | — | 8.07 |
| D |  |  |  | — |

Figure 10:
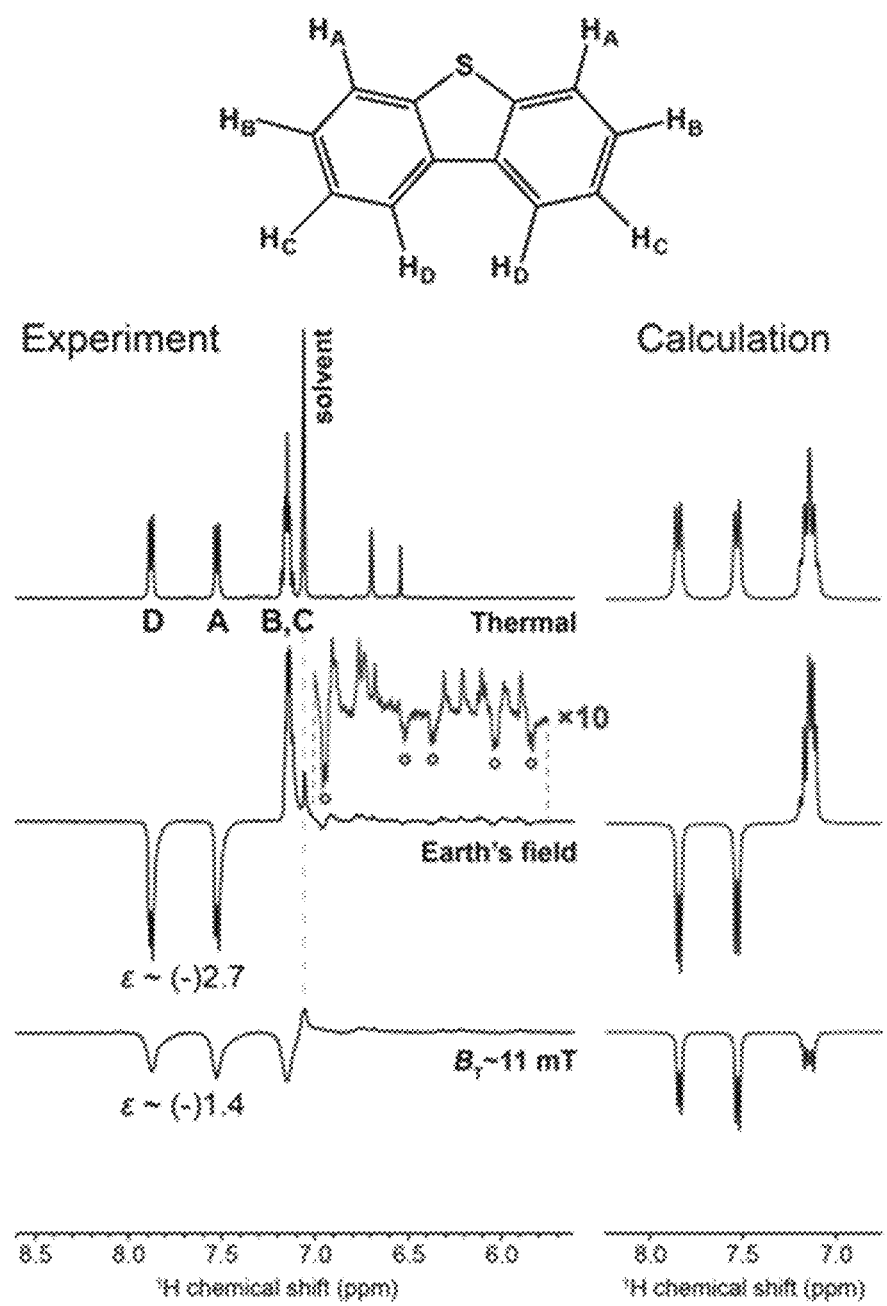
FIG. 10 shows the SABRE hyperpolarization of dibenzothiophene. $^1$H NMR spectrum of dibenzothiophene at thermal equilibrium of nuclear spin polarization (top spectrum). $^1$H NMR spectrum of dibenzothiophene after SABRE hyperpolarization process conducted in the Earth's magnetic field, the process aimed at the pseudo-singlet state overpopulation (middle spectrum) (Theis T et al. *Sci. Adv.* 2016, 2, e1501438). The NMR resonances labeled with δ correspond to catalyst-bound dibenzothiophene species. NMR spectrum of dibenzothiophene after performing the SABRE hyperpolarization process at $B_T$~11 mT (bottom spectrum).
Figure 11:
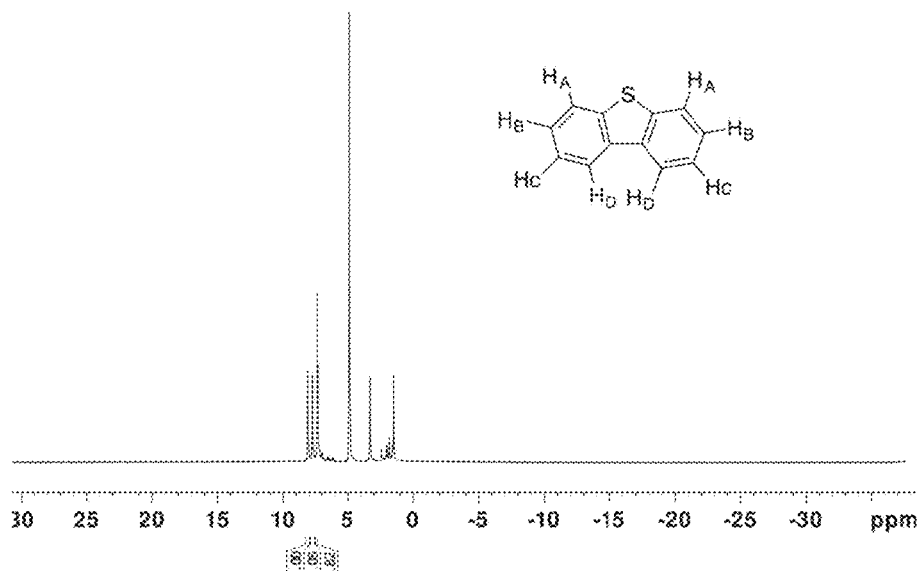
FIG. 11 is a high-resolution thermal $^1$H spectrum NMR spectrum of dibenzothiophene (0.060 M) and Ir-IMes SABRE catalyst (0.004) M) in benzene-$d_6$: methanol-$d_4$ (3:7).
Figure 12:
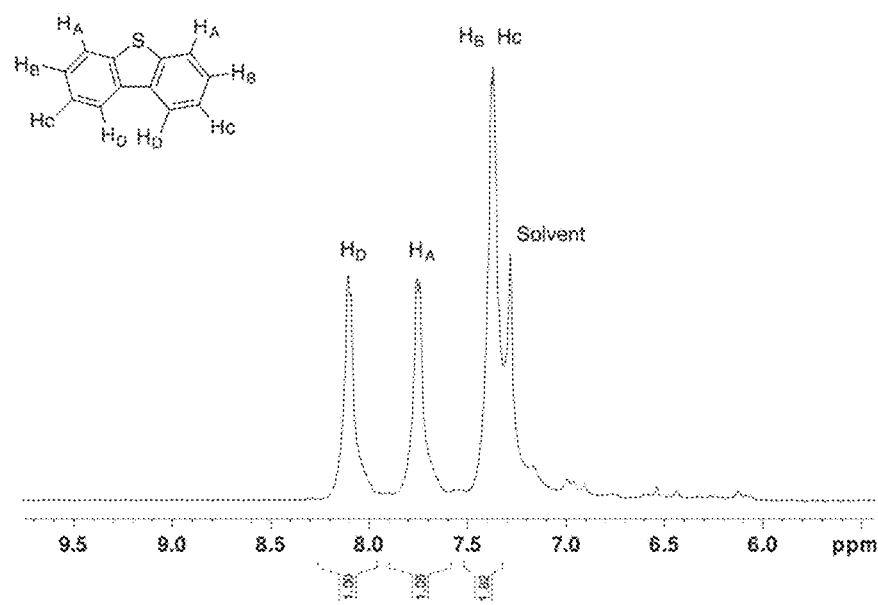
FIG. 12 is a high-resolution thermal $^1$H spectrum NMR spectrum of dibenzothiophene (0.060 M) and Ir-IMes SABRE catalyst (0.0040 M) in benzene-$d_6$: methanol-$d_4$. (3:7, aromatic region).
Figure 13:
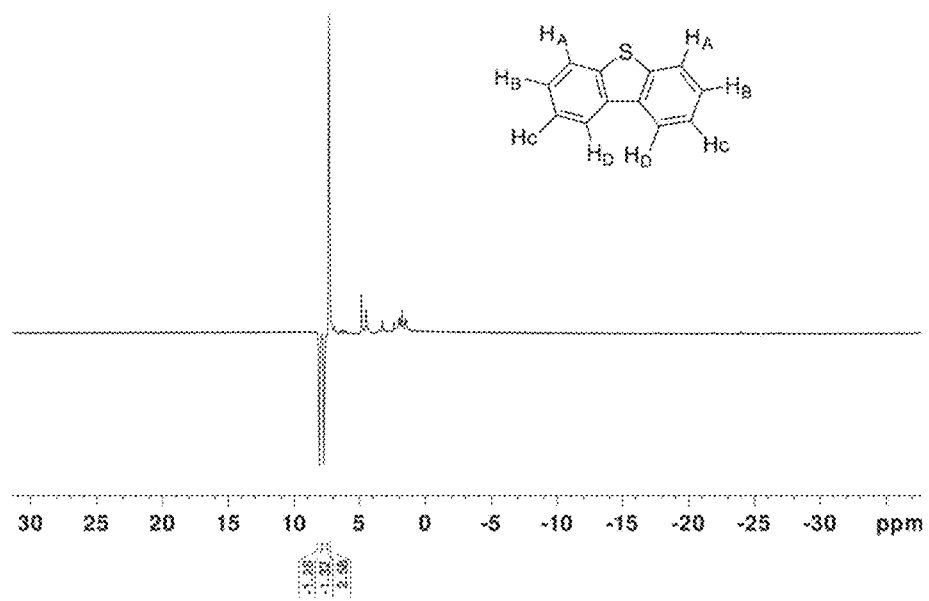
FIG. 13 is a high-resolution $^1$H spectrum NMR spectrum of hyperpolarized (HP) dibenzothiophene (0.060 M) and Ir-IMes SABRE catalyst (0.0040 M) in benzene-$d_6$: methanol-$d_4$. (3:7). SABRE hyperpolarization is performed in the Earth's magnetic field using ~50% para-$H_2$ gas.
Figure 14:
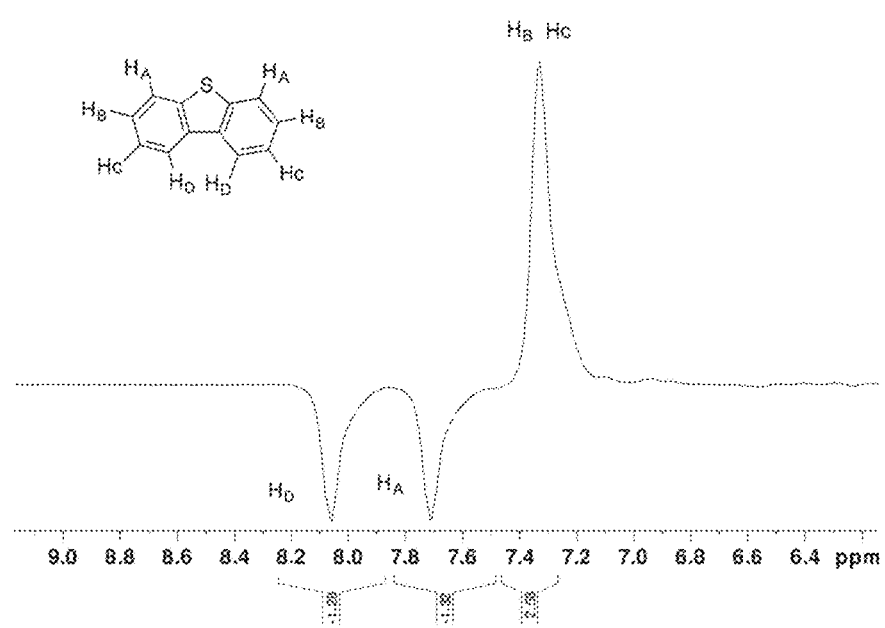
FIG. 14 is a high-resolution $^1$H spectrum NMR spectrum of hyperpolarized dibenzothiophene (0.060 M) and Ir-IMes SABRE catalyst (0.0040 M) in benzene-$d_6$: methanol-$d_4$. (3:7, aromatic region). SABRE hyperpolarization is performed in the Earth's magnetic field using ~50% para-$H_2$ gas.
Figure 15:
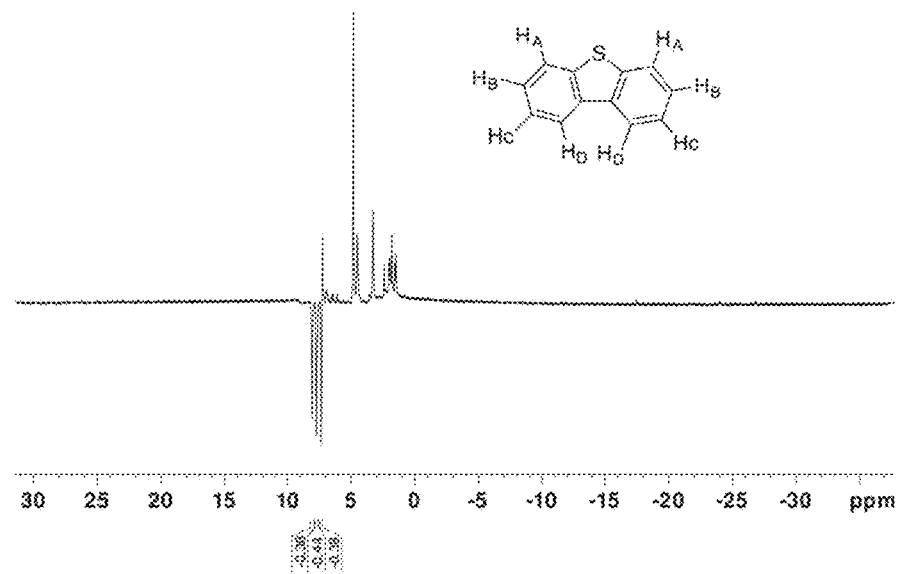
FIG. 15 is a high-resolution $^1$H spectrum NMR spectrum of hyperpolarized dibenzothiophene (0.060 M) and Ir-IMes SABRE catalyst (0.0040 M) in benzene-$d_6$: methanol-$d_4$ (3:7). SABRE hyperpolarization is performed in the magnetic field of ~11 mT using ~50% para-$H_2$ gas.
Figure 16:
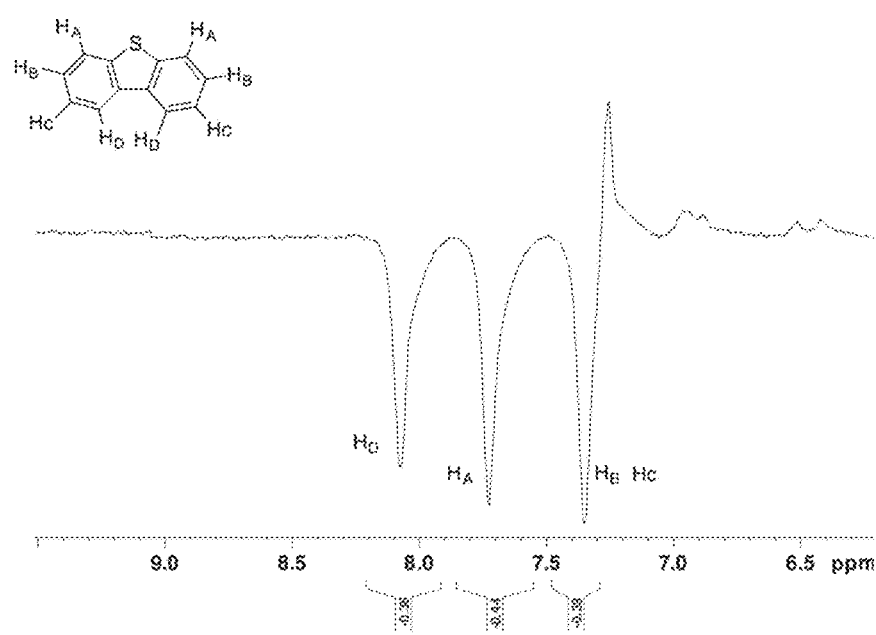
FIG. 16 is a high-resolution $^1$H spectrum NMR spectrum of hyperpolarized dibenzothiophene (0.060 M) and Ir-IMes SABRE catalyst (0.0040 M) in benzene-$d_6$: methanol-$d_4$. (3:7, aromatic region). SABRE hyperpolarization is performed in the magnetic field of ~11 mT using ~50% para-$H_2$ gas: $\varepsilon_{HD}$~(−)1.4, $\varepsilon_{HA}$~(−)1.4, $\varepsilon_{HB}$~(−)1.4.
Figure 17:
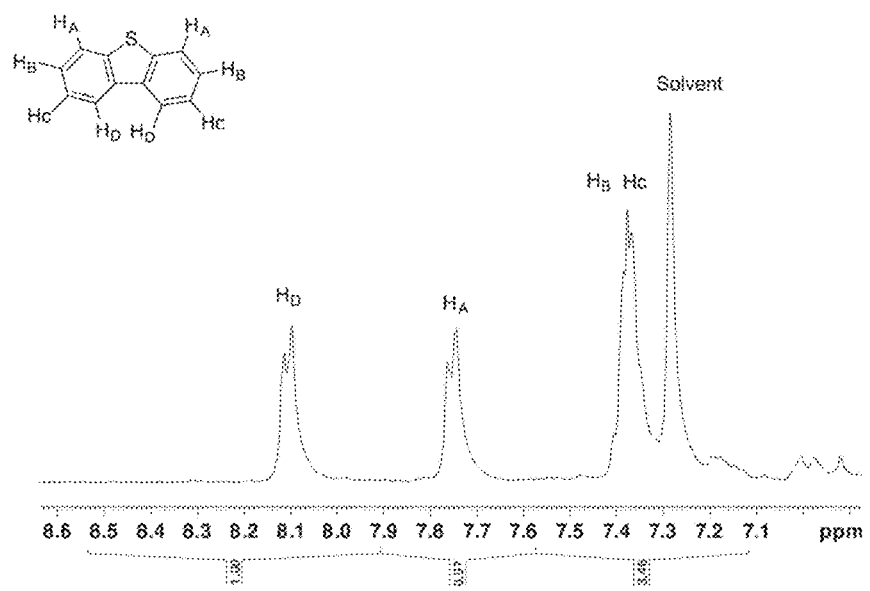
FIG. 17 is a high-resolution thermal $^1$H spectrum NMR spectrum of dibenzothiophene (0.015 M) and Ir-IMes SABRE catalyst (0.0040 M) in benzene-$d_6$: methanol-$d_4$. (3:7, aromatic region).
Figure 18:
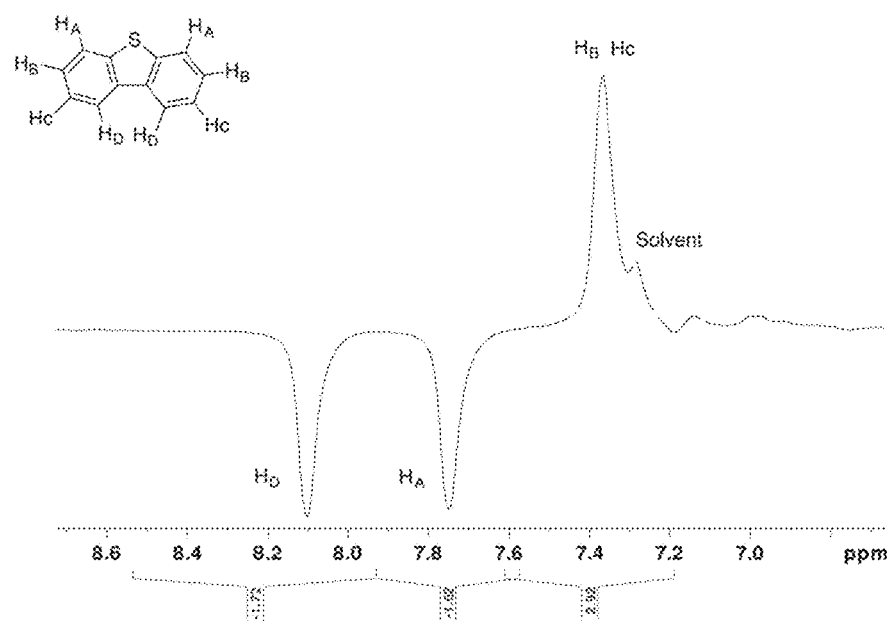
FIG. 18 is a high-resolution $^1$H spectrum NMR spectrum of hyperpolarized dibenzothiophene (0.015 M) and Ir-IMes SABRE catalyst (0.0040 M) in benzene-$d_6$: methanol-$d_4$. (3:7, aromatic region). SABRE hyperpolarization is performed in the Earth's magnetic field using ~50% para-$H_2$ gas: $\varepsilon_{HD}$~(−)2.7, $\varepsilon_{HA}$~(−)2.6.
Figure 19:
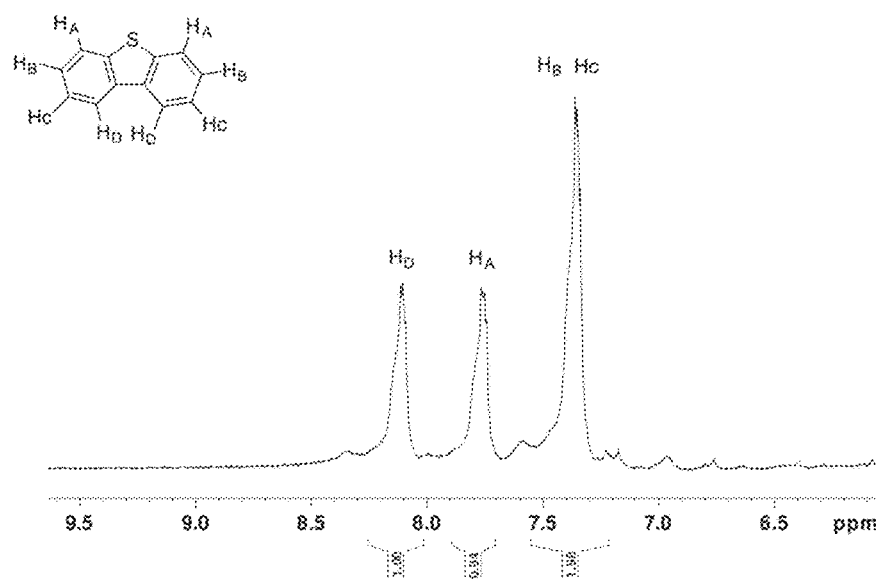
FIG. 19 is a high-resolution thermal $^1$H spectrum NMR spectrum of dibenzothiophene (0.030 M) and Ir-IMes SABRE catalyst (0.0040 M) in benzene-$d_6$: methanol-$d_4$. (3:7, aromatic region).
Figure 20:
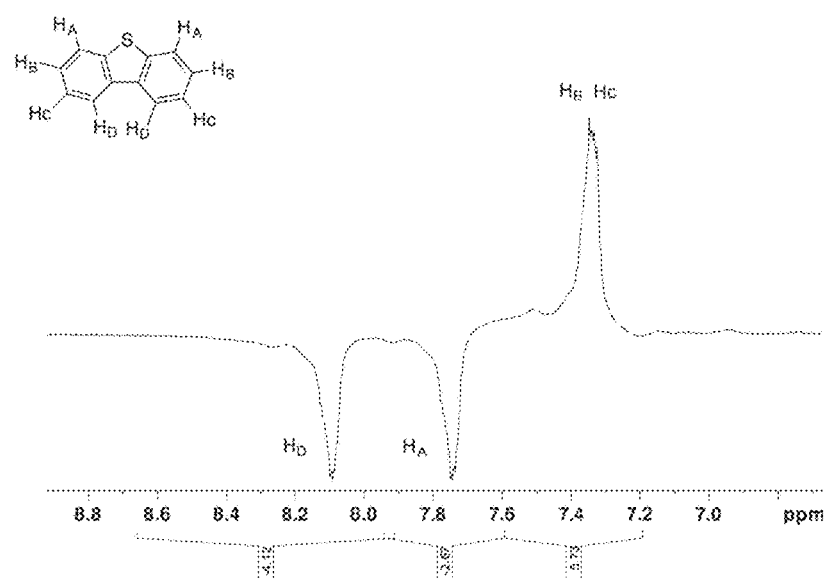
FIG. 20 is a high-resolution $^1$H spectrum NMR spectrum of hyperpolarized dibenzothiophene (0.030 M) and Ir-IMes SABRE catalyst (0.0040 M) in benzene-$d_6$: methanol-$d_4$. (3:7, aromatic region). SABRE hyperpolarization is performed in the fringe field of the 9.4 T NMR using ~50% para-$H_2$ gas. $\varepsilon_{HD}$~(−)5.1, $\varepsilon_{HA}$~(−)3.7, $\varepsilon_{B,C}$~(+)1.9.

When $B_T$ is roughly matched to the spin-spin coupling ($J_{H-H}$) between nascent parahydrogen-derived hydride protons on the metal center (Theis T et al. *J. Am. Chem. Soc.* 2015, 137, 1404-1407; Eshuis N et al. *J. Magn. Reson.* 2016, 265, 59-66), a coherent polarization transfer from hydride protons to the protons of the substrate molecule occurs (FIG. 10, bottom spectrum)—in accord with conventional SABRE of N-heterocycles (Adams R W et al. *Science* 2009, 323, 1708-1711: Adams R W et al *J. Chem. Phys.* 2009, 131, 194505: Pravdivtsev A N et al. *ChemPhysChem* 2013, 14, 3327-3331). Once polarization transfer occurs on the Ir-hexacoordinate complex, the hyperpolarized substrate molecules and hydride hydrogens exchange with free substrate and parahydrogen in solution, allowing the SABRE hyperpolarization cycle to continue as it reaches the maximum hyperpolarization level at steady state (which typically occurs in seconds) (Adams R W et al. *Science* 2009, 323, 1708-1711: Adams R W et al. *J. Chem. Phys.* 2009, 131, 194505). The characteristic phase shift of the hyperpolarized $^1$H resonances of dibenzothiophene can be seen in the bottom spectrum of FIG. 10. When $B_T$ is mismatched, e. g. when the SABRE exchange process is conducted in the Earth's magnetic field of ~50 µT, polarization transfer still occurs (Theis T et al. *Sci. Adv.* 2016, 2, e1501438)— although pseudo-singlet spin-states are being overpopulated, which is manifested by the opposite (absorptive vs. emissive) phases of the $H_{A,D}$ and $H_{B,C}$ $^1$H NMR resonances (FIG. 10, middle spectrum). The inverted resonances assigned to catalyst-bound substrate species are detected (FIG. 10, middle spectrum, inset) indicating the chemical exchange of S-heterocycles on the time scale similar to that seen in SABRE of N-heterocycles.

$^1$H SABRE enhancements (ε, Table 1) were calculated by comparing integral signal intensities of corresponding NMR peaks of the spectra of hyperpolarized ($S_{HP}$) and thermally polarized ($S_{THER}$) conditions according to:

$$\varepsilon = (S_{HP} - S_{THER})/S_{THER}$$

The NMR signal enhancements derived from SABRE hyperpolarization processes for sulfur-containing compounds (S-SABRE) were relatively modest (ca. (−)5 fold—roughly 2-3 orders of magnitude lower than the best $^1$H polarization enhancements reported to date for this catalyst (Cowley M J et al. *J. Am. Chem. Soc.* 2011, 133, 6134-6137). Robust gains in S-SABRE efficiency can likely be obtained by (i) employing near 100% parahydrogen (vs. ~50% parafraction which reduced the apparent enhancements by approximately a factor of 3), (ii) reducing the concentration of the S-substrate (Barskiy D A et al. *Phys. Chem. Chem. Phys.* 2016, 18, 89-93), and (iii) catalyst pre-activation with small molecules (e. g. pyridine) resulting in better Ir center accessibility, because the axial non-exchangeable site (FIG. 8) would be occupied by a less bulky ligand (Shchepin R V et al. *Bioconjugate Chem.* 2016, 27, 878-882: Eshuis N et al. *J. Am. Chem. Soc.* 2014, 136, 2695-2698). However, the design of more efficient SABRE catalysts geared towards hyperpolarization of sulfur—rather than nitrogen—containing heterocycles will likely be required in the future to bring S-SABRE hyperpolarization efficiency on par with conventional SABRE of N-heterocycles, which has been successfully employed for quantitative trace analysis below 1 mM (corresponding to <0.1 ppm detection capability) (Eshuis N et al. *Angew. Chem. Int. Ed.* 2015, 54, 1481-1484; Eshuis N et al. *J. Am. Chem. Soc.* 2014, 136, 2695-2698).

Figure 21:
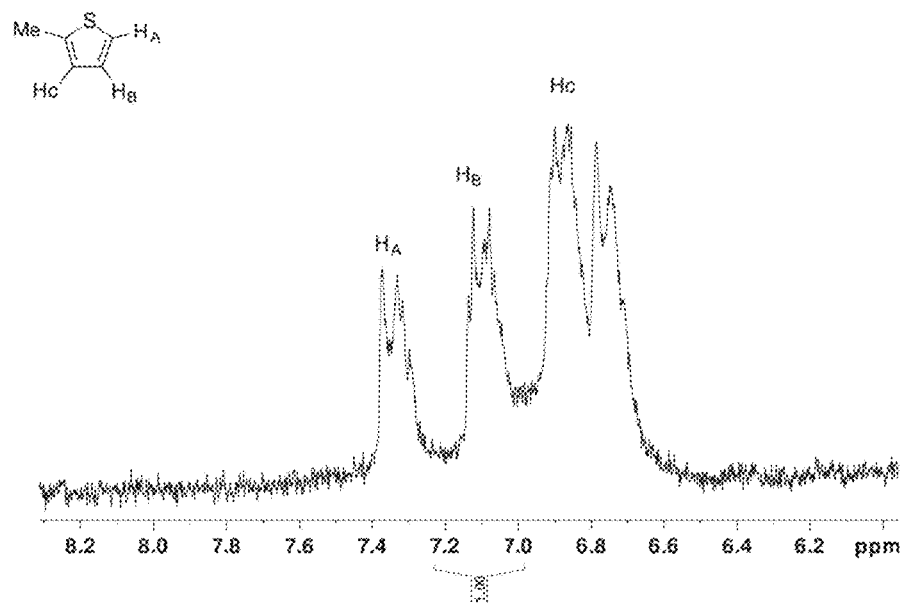
FIG. 21 is a thermal $^1$H spectrum NMR spectrum of 2-methylthiophene (0.030 M) and Ir-IMes SABRE catalyst (0.0040 M) in benzene-$d_6$: methanol-$d_4$. (3:7, aromatic region).
Figure 22:
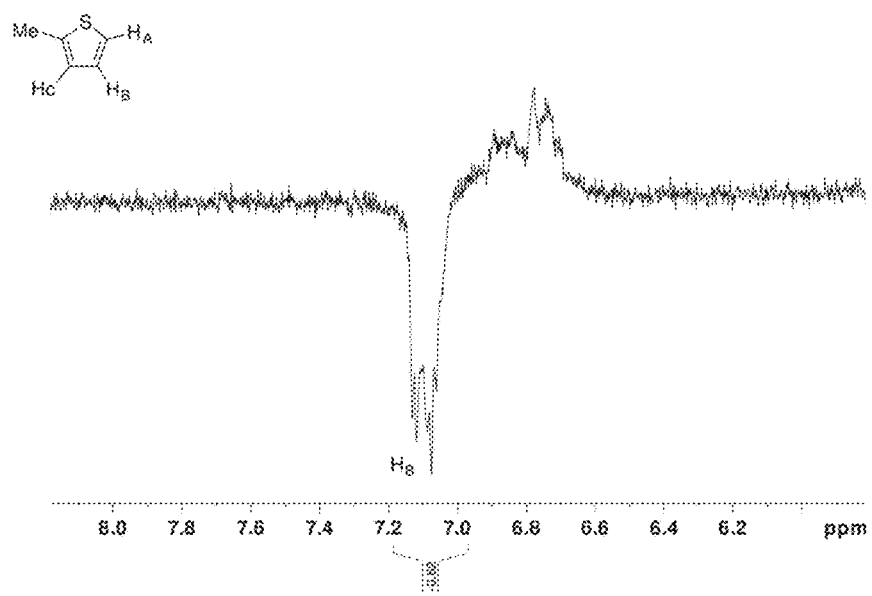
FIG. 22 is a $^1$H spectrum NMR spectrum of hyperpolarized 2-methylthiophene (0.030 M) and Ir-IMes SABRE catalyst (0.0040 M) in benzene-$d_6$: methanol-$d_4$. (3:7, aromatic region): $\varepsilon_{HB}$~(−)1.6.

Corresponding thermal $^1$H NMR and $^1$H SABRE hyperpolarization spectra are provided for methylthiophene in FIG. 21 and FIG. 22, respectively. Taken together with dibenzothiophene's SABRE hyperpolarization feasibility (FIG. 10), the results discuss herein indicate that the SABRE hyperpolarization technique can be generally applicable to thiophene-based substituted heterocycles, common impurities in crude oil (Kropp K G and Fedorak P M. *Can. J. Microbiol.* 1998, 44, 605-622). SABRE-based NMR sensing could therefore potentially provide a convenient means of detecting the presence and structure of sulfur-heterocycles in crude oil samples in the future, because (1) it is an instrumentally non-demanding technique; (2) the hyperpolarized NMR resonances have an opposite phase with respect to the rest of the protons in the spectrum (Adams R W et al. *Science* 2009, 323, 1708-1711; Barskiy D A et al. *J. Am. Chem. Soc.* 2014, 136, 3322-3325); and (3) the SABRE effect is likely to be at least partially selective for the heterocyclic compounds found in oil.

Although conventional PHIP can be applied for detection of thiophenes (Salnikov O G et al. *ChemCatChem* 2015, 7, 3508-3512) and potentially other sulfur-containing compounds with unsaturated chemical bonds, that parahydrogen-based hyperpolarization technique relies on pairwise addition of p-H$_2$, and therefore leads to chemical modification of the substrate-rendering the NMR spectral interpretation significantly more challenging compared to the SABRE approach. Moreover, only two hyperpolarized protons can be typically visualized with the conventional PHIP approach, whereas the SABRE method demonstrated here allows enhancing multiple proton sites. Furthermore, the conventional hydrogenative PHIP technique is an irreversible process (Bowers C R and Weitekamp D P. *Phys. Rev. Lett.* 1986, 57, 2645-2648; Bowers C R and Weitekamp D P. *J. Am. Chem. Soc.* 1987, 109, 5541-5542), whereas SABRE allows repeating the hyperpolarization process multiple times (Hovener J B et al. *Nat. Commun.* 2013, 4, 5), which is useful in the context of multi-dimensional NMR spectroscopy (Eshuis N et al. *Angew. Chem. Int. Ed.* 2015, 54, 1481-1484).

NMR hyperpolarization via Signal Amplification by Reversible Exchange (SABRE) was employed to investigate the feasibility of enhancing the NMR detection sensitivity of sulfur-heterocycles (specifically 2-methylthiophene and dibenzothiophenes), a family of compounds typically found in petroleum and refined petroleum products. It was shown that substituted (in ortho-position) thiophenes are amenable to SABRE hyperpolarization with an already-available catalyst (and an easily-created source of ~50% p-H$_2$ using liquid N2 cooling). Moreover, hyperpolarization of relatively distant protons (up to four chemical bonds away from sulfur, FIG. 10) is feasible. This result indicates that SABRE can provide rich structural information, because multiple protons of the same sulfur-containing heterocycle can be hyperpolarized and used as spectral signatures for detecting a wide range of compounds simultaneously. SABRE hyperpolarization of sulfur-heterocycles (conducted in seconds) offers potential advantages of providing structural information about sulfur-containing contaminants in petroleum, thereby informing petroleum purification and refining to minimize sulfur content in refined products such as gasoline. Furthermore, the extension of SABRE to the new class of heterocycles demonstrated here may be synergistic with the recent development of heterogeneous SABRE catalysis (Shi F et al. *Angew. Chem. Int. Ed.* 2014, 53, 7495-7498; Shi F et al. *J. Phys. Chem. C* 2015, 119, 7525-7533).

Moreover, NMR spectroscopy sensitivity gains endowed by hyperpolarization (Suefke M et al. Nat. Phys. 2015, 767-771; Coffey A M et al. *J. Magn. Reson.* 2013, 237, 169-174) potentially allows for performing structural assays, low-field NMR SABRE spectroscopy, and MRI imaging using inexpensive, portable, low-magnetic-field (ca. 1 T) high-resolution NMR spectrometers (Hovener J B et al. *Nat.*

*Commun.* 2013, 4, 5; Coffey A M et al. *Anal. Chem.* 2014, 86, 9042-9049; Gloggler S et al. *Phys. Chem. Chem. Phys.* 2011, 13, 13759-13764). Finally, the use of low-field NMR spectroscopy for selective detection of S-SABRE hyperpolarized substances in complex mixtures may benefit from the reduced signal background originating from other more abundant but non-hyperpolarized substances.

Other advantages which are obvious and which are inherent to the disclosure will be evident to one skilled in the art. It will be understood that certain features and sub-combinations are of utility and may be employed without reference to other features and sub-combinations. This is contemplated by and is within the scope of the claims. Since many possible embodiments may be made without departing from the scope thereof, it is to be understood that all matter herein set forth or shown in the accompanying drawings is to be interpreted as illustrative and not in a limiting sense.

The methods of the appended claims are not limited in scope by the specific methods described herein, which are intended as illustrations of a few aspects of the claims and any methods that are functionally equivalent are intended to fall within the scope of the claims. Various modifications of the methods in addition to those shown and described herein are intended to fall within the scope of the appended claims. Further, while only certain representative method steps disclosed herein are specifically described, other combinations of the method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such components, and the like.

"Optional" or "optionally" means that the subsequently described event or circumstance can or cannot occur, and that the description includes instances where the event or circumstance occurs and instances where it does not.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB. AAA, AB, BBC, AAABCCCC, CBBAAA, CABABB, and so forth. The skilled artisan will understand that typically there is no limit on the number of items or terms in any combination, unless otherwise apparent from the context.

What is claimed is:

1. A method of detecting a sulfur-containing compound in a sample, comprising:
    contacting the sample comprising the sulfur-containing compound with parahydrogen and a catalyst to form a mixture, thereby transferring a spin order from the parahydrogen to the sulfur-containing compound and hyperpolarizing the sulfur-containing compound during a temporary association of the parahydrogen, the sulfur-containing compound, and the catalyst; and
    performing an NMR measurement on the mixture comprising the hyperpolarized sulfur-containing compound to detect the hyperpolarized sulfur-containing compound;
    wherein the temporary association of the parahydrogen, the sulfur-containing compound, and the catalyst has terminated before the NMR measurement is performed.

2. The method of claim 1, wherein the spin order is transferred spontaneously.

3. The method of claim 1, wherein the spin order is transferred non-spontaneously.

4. The method of claim 1, wherein performing the NMR measurement comprises using a magnetic field having a strength of from $1 \times 10^{-7}$ Tesla (T) to 100 T.

5. The method of claim 4, wherein the magnetic field is the Earth's magnetic field.

6. The method of claim 1, wherein the sulfur-containing compound has a chemical identity, and the chemical identity of the sulfur-containing compound before the contacting step is the same as the chemical identity of the sulfur-containing compound in the mixture subjected to the NMR measurement step.

7. The method of claim 1, wherein the sulfur-containing compound comprises an organosulfur compound.

8. The method of claim 7, wherein the organosulfur compound is substituted with one or more methyl substituents, one or more ethyl substituents, or combinations thereof.

9. The method of claim 7, wherein the organosulfur compound comprises a sulfur-containing heterocycle.

10. The method of claim 9, wherein the sulfur-containing heterocycle comprises a thiophene compound.

11. The method of claim 10, wherein the thiophene compound comprises thiophene, benzothiophene, dibenzothiophene, or combinations thereof, any of which is optionally substituted with one or more methyl substituents, one or more ethyl substituents, or combinations thereof.

12. The method of claim 1, wherein the sulfur-containing compound comprises sulfuric acid, sulfur dioxide, carbon disulfide, methyl sulfide, carbonyl sulfide, hydrogen sulfide, or combinations thereof.

13. The method of claim 1, wherein the sulfur-containing compound has a concentration of from $10^{-9}$ M to 10 M.

14. The method of claim 1, wherein the catalyst comprises a metal complex.

15. The method of claim 1, wherein the catalyst comprises an iridium complex.

16. The method of claim 1, wherein the sulfur-containing compound is present in an amount in the sample and detecting the hyperpolarized sulfur-containing compound comprises quantifying the amount of the sulfur-containing compound in the sample.

17. The method of claim 1, wherein the hyperpolarized sulfur-containing compound has an NMR signal with a phase that is 180 degrees different than an NMR signal from the mixture.

18. The method of claim 1, wherein the sample comprises a hydrocarbon fluid.

19. The method of claim 1, wherein the sample comprises the sulfur-containing compound and a solvent, the solvent being methanol, ethanol, n-butanol, isopropanol, n-propanol, acetic acid, water, benzene, toluene, heptane, hexane, or combinations thereof.

20. The method of claim 1, wherein the mixture consists of the sample, parahydrogen, and the catalyst.

* * * * *